US009506938B2

(12) United States Patent
Coller et al.

(10) Patent No.: US 9,506,938 B2
(45) Date of Patent: *Nov. 29, 2016

(54) METHODS FOR MEASURING PLATELET REACTIVITY OF INDIVIDUALS TREATED WITH DRUG ELUTING STENTS

(75) Inventors: Barry Coller, New York, NY (US); Dennis Durbin, Solana Beach, CA (US)

(73) Assignee: ACCUMETRICS, INC., San Diego, CA (US)

( * ) Notice: Subject to any disclaimer, the term of this patent is extended or adjusted under 35 U.S.C. 154(b) by 1031 days.

This patent is subject to a terminal disclaimer.

(21) Appl. No.: 12/598,581

(22) PCT Filed: May 1, 2008

(86) PCT No.: PCT/US2008/062297
§ 371 (c)(1),
(2), (4) Date: Mar. 30, 2010

(87) PCT Pub. No.: WO2008/137600
PCT Pub. Date: Nov. 13, 2008

(65) Prior Publication Data
US 2010/0184084 A1  Jul. 22, 2010

Related U.S. Application Data

(63) Continuation of application No. 11/742,684, filed on May 1, 2007, now abandoned.

(51) Int. Cl.
*G01N 33/86* (2006.01)

(52) U.S. Cl.
CPC ......... *G01N 33/86* (2013.01); *G01N 2800/222* (2013.01); *G01N 2800/226* (2013.01); *G01N 2800/50* (2013.01)

(58) Field of Classification Search
USPC .......................................................... 435/7.2
See application file for complete search history.

(56) References Cited

U.S. PATENT DOCUMENTS

| | | | |
|---|---|---|---|
| 3,518,057 A | 6/1970 | Giordano | |
| 3,694,161 A | 9/1972 | Kleszynski et al. | |
| 3,817,837 A | 6/1974 | Rubenstein et al. | |
| 4,051,236 A * | 9/1977 | Harris et al. .................. | 424/532 |
| 4,066,360 A | 1/1978 | Breddin | |
| 4,339,452 A | 7/1982 | Hara et al. | |
| 4,529,561 A | 7/1985 | Hunt et al. | |
| 4,619,904 A | 10/1986 | Giaever et al. | |
| 4,634,681 A | 1/1987 | Giaever et al. | |
| 4,820,836 A | 4/1989 | Mori et al. | |
| 4,948,961 A | 8/1990 | Hillman et al. | |
| 5,023,233 A | 6/1991 | Nutt et al. | |
| 5,066,592 A | 11/1991 | Huang et al. | |
| 5,242,810 A | 9/1993 | Maraganore et al. | |
| 5,246,832 A | 9/1993 | Michelson et al. | |
| 5,266,462 A | 11/1993 | Hemker et al. | |
| 5,284,751 A | 2/1994 | Frelinger, III et al. | |
| 5,427,913 A | 6/1995 | Shaw et al. | |
| 5,455,228 A | 10/1995 | Coller et al. | |
| 5,486,361 A | 1/1996 | Gralnick | |
| 5,523,238 A | 6/1996 | Varon et al. | |
| 5,530,114 A | 6/1996 | Bennett | |
| 5,753,517 A | 5/1998 | Brooks et al. | |
| 5,763,199 A | 6/1998 | Coller | |
| 5,854,005 A | 12/1998 | Coller | |
| D409,758 S | 5/1999 | Warden et al. | |
| 5,922,551 A * | 7/1999 | Durbin et al. ............... | 435/7.21 |
| 5,952,006 A | 9/1999 | Drizen et al. | |
| 5,972,712 A | 10/1999 | Baugh et al. | |
| 5,989,578 A * | 11/1999 | Bernat et al. ................. | 424/422 |
| 6,016,712 A | 1/2000 | Warden et al. | |
| 6,043,871 A | 3/2000 | Solen et al. | |
| 6,063,847 A | 5/2000 | Chackalamannil et al. | |
| 6,093,370 A | 7/2000 | Yasuda et al. | |
| 6,210,904 B1 | 4/2001 | Bednar et al. | |
| 6,326,380 B1 | 12/2001 | Chackalamannil et al. | |
| 6,376,242 B1 * | 4/2002 | Hanson ......................... | 435/334 |
| 6,387,645 B1 * | 5/2002 | Ford et al. ...................... | 435/21 |

(Continued)

FOREIGN PATENT DOCUMENTS

| | | |
|---|---|---|
| EP | 0133464 | 2/1985 |
| EP | 0165681 | 12/1985 |

(Continued)

OTHER PUBLICATIONS

Beer, J. H. et al. "Immobilized Arg-Gly-Asp (RGD) Peptides of Varying Lengths as Structural Probes of the Platelet Glycoprotein IIb/IIIa Receptor" Blood, W. B. Saunders Company, Orlando, FL, vol. 79, No. 1, Jan. 1, 1992, p. 117-128, XP002988010.

(Continued)

*Primary Examiner* — Lora E Barnhart Driscoll
(74) *Attorney, Agent, or Firm* — Cooley LLP

(57) ABSTRACT

A method is provided for measuring inhibition of platelet reactivity in an individual treated with a drug-eluting stent (DES). First, a blood sample is obtained from an individual treated with a DES and a P2Y12 antagonist. The blood sample is then mixed with particles comprising an attached GPIIb/IIIa receptor ligand, adenosine diphosphate (ADP) and prostaglandin E1 (PGE1). The mixture is incubated under conditions suitable for agglutinating particles, and platelet-mediated agglutination is assessed in the mixture. The absence or reduction of agglutination indicates that the individual treated with a DES has reduced platelet reactivity. Also provided is a kit for measuring inhibition of platelet aggregation by a P2Y12 receptor antagonist that includes a GPIIb/IIIa receptor ligand immobilized on a particle, adenosine diphosphate (ADP), prostaglandin E1 (PGE1), an anticoagulant, and a buffer to maintain the anticoagulated blood in a condition suitable for platelet aggregation.

20 Claims, 4 Drawing Sheets

(56) References Cited

U.S. PATENT DOCUMENTS

| | | | |
|---|---|---|---|
| 6,531,150 | B1 | 3/2003 | Sunohara et al. |
| 6,555,064 | B2 | 4/2003 | Baugh et al. |
| 6,589,992 | B2 | 7/2003 | Uckun |
| 6,596,191 | B2 | 7/2003 | Sakamoto et al. |
| 6,645,987 | B2 | 11/2003 | Chackalamannil et al. |
| 6,841,354 | B2 | 1/2005 | Soslau |
| 6,894,065 | B2 | 5/2005 | ChackalamanniL et al. |
| 7,037,920 | B2 | 5/2006 | Chackalamannil et al. |
| 7,205,115 | B2 | 4/2007 | Mchugh et al. |
| 7,244,730 | B2 | 7/2007 | Suzuki et al. |
| 7,304,083 | B2 | 12/2007 | Suzuki et al. |
| 7,595,169 | B2 | 9/2009 | Swaim et al. |
| 7,790,362 | B2 | 9/2010 | Coller et al. |
| 8,574,828 | B2 | 11/2013 | Coller et al. |
| 2002/0022637 | A1 | 2/2002 | Li et al. |
| 2002/0061844 | A1 | 5/2002 | Baell et al. |
| 2002/0077693 | A1* | 6/2002 | Barclay et al. ............ 623/1.13 |
| 2002/0103107 | A1 | 8/2002 | Soslau |
| 2003/0124615 | A1* | 7/2003 | Ens ............................ 435/7.1 |
| 2003/0148264 | A1 | 8/2003 | Held et al. |
| 2003/0231878 | A1 | 12/2003 | Shigeura |
| 2004/0106988 | A1 | 6/2004 | Summers |
| 2005/0004197 | A1 | 1/2005 | Suzuki et al. |
| 2005/0031616 | A1 | 2/2005 | Coller et al. |
| 2005/0191333 | A1* | 9/2005 | Hsu ............................ 424/424 |
| 2006/0246527 | A1 | 11/2006 | Mchugh et al. |
| 2006/0246528 | A1 | 11/2006 | Swaim et al. |
| 2007/0243632 | A1 | 10/2007 | Coller et al. |
| 2008/0299587 | A1 | 12/2008 | Durbin |
| 2011/0065125 | A1 | 3/2011 | Coller et al. |
| 2011/0081657 | A1 | 4/2011 | Coller et al. |
| 2014/0234859 | A1 | 8/2014 | Coller et al. |

FOREIGN PATENT DOCUMENTS

| | | |
|---|---|---|
| EP | 0964046 | 12/1999 |
| EP | 1025842 | 8/2000 |
| JP | 07-203994 | 8/1995 |
| WO | WO 9208982 | 5/1992 |
| WO | WO 9214750 | 9/1992 |
| WO | WO 95/00544 | 1/1995 |
| WO | WO 9527209 | 10/1995 |
| WO | WO 96/03655 | 2/1996 |
| WO | WO 9610749 | 4/1996 |
| WO | WO 98/41868 | 9/1998 |
| WO | WO 99/14595 | 3/1999 |
| WO | WO 99/22719 | 5/1999 |
| WO | WO 99/43809 | 9/1999 |
| WO | WO 00/25140 | 5/2000 |
| WO | WO 2000/073792 | 12/2000 |
| WO | WO 2002/036631 | 5/2002 |
| WO | WO 03/004604 | 1/2003 |
| WO | WO 2004/036226 | 4/2004 |
| WO | 2005007868 A | 1/2005 |
| WO | WO 2006/115844 | 11/2006 |
| WO | WO 2006/116699 | 11/2006 |
| WO | WO 2007/007588 | 1/2007 |
| WO | WO 2008/137600 | 11/2008 |
| WO | WO 2008/137673 | 11/2008 |
| WO | WO 2009/067744 | 6/2009 |

OTHER PUBLICATIONS

Gurbel, et al., "Clopidogrel Effect on Platelet Reactivity in Patients with Stent Thrombosis" Journal of the American College of Cardiology, Elsevier, New York, NY, US, vol. 46, No. 10, Nov. 15, 2005, p. 1827-1832, XP005158524.
International Preliminary Report on Patentability and Written Opinion for corresponding International Application No. PCT/2008/062297, mailed Nov. 12, 2009.
International Search Report for corresponding International Application No. PCT/2008/062297, mailed Aug. 6, 2008.
Office Action for corresponding EP Application 08754988.7 mailed Feb. 24, 2010.
Supplementay European Search Report for European Application No. 04756747, mailed Jul. 17, 2009.
Office Action for European Application No. 04756747, mailed Nov. 11, 2009.
Office Action for U.S. Appl. No. 10/886,155, mailed Oct. 26, 2006.
Office Action for U.S. Appl. No. 10/886,155, mailed Jul. 9, 2007.
Office Action for U.S. Appl. No. 10/886,155, mailed Aug. 8, 2007.
Office Action for U.S. Appl. No. 10/886,155, dated Aug. 7, 2008.
Office Action for U.S. Appl. No. 10/886,155, mailed Jan. 16, 2009.
Office Action for U.S. Appl. No. 10/886,155, mailed Jul. 24, 2009.
International Preliminary Report on Patentabilty for International Application No. PCT/US2004/21785, dated Jan. 9, 2006.
International Search Report and Written Opinion for International Application No. PCT/US2004/21785, mailed Jun. 13, 2005.
Office Action for Chinese Application No. 200880022878.8 dated Jun. 5, 2012.
Office Action for Japanese Application No. 2010-506656, dated Jul. 5, 2012.
Office Action for U.S. Appl. No. 12/876,730, mailed Jun. 18, 2012.
Office Action for U.S. Appl. No. 12/876,730, mailed Jan. 7, 2013.
Supplementay European Search Report for European Application No. 06769917 mailed Jul. 9, 2008.
Office Action for Japanese Application No. 2008-509177, dated Dec. 5, 2011.
Office Action for Japanese Application No. 2008-509177, dated Jul. 5, 2012.
Office Action for Korean Application No. 10-2007-7027482, dated Nov. 13, 2012.
Office Action for U.S. Appl. No. 11/411,239, dated Jun. 25, 2008.
International Search Report and Written Opinion for International Application No. PCT/US2006/016289, mailed Oct. 31, 2006.
International Preliminary Report on Patentability for International Application No. PCT/US2006/016289, dated Oct. 30, 2007.
Examination Report for Australian Application No. 2006240257, dated Apr. 6, 2011.
Office Action for Chinese Patent Application No. 200680022849.2, dated Apr. 22, 2011.
Office Action for Chinese Patent Application No. 200680022849.2, dated Nov. 11, 2010.
Office Action for European Application No. 06750226, mailed Aug. 20, 2009.
Office Action for European Application No. 06750226, mailed May 25, 2011.
Extended European Search Report for European Application No. 06750226, mailed Aug. 27, 2008.
Office Action for Japanese Application No. 2008-508905, dated Feb. 1, 2011.
Office Action for Korean Application No. 10-2007-7027636, dated Sep. 25, 2012.
Office Action for U.S. Appl. No. 11/119,360, dated Jan. 12, 2006.
Office Action for U.S. Appl. No. 11/119,360, dated Sep. 12, 2006.
International Search Report and Written Opinion for International Application No. PCT/US2006/014136, mailed Aug. 31, 2006.
European Search Report for European Application No. EP 10193726.6, mailed May 18, 2011.
Examination Report for European Application No. 10193726.6, dated Feb. 27, 2012.
Office Action for Chinese Application No. 200880014577.0, dated Apr. 12, 2012.
Notice of Opposition for European Application No. 08755007.5, dated Feb. 2, 2013.
Office Action for European Application No. 08755007 mailed Feb. 3, 2010.
Office Action for Japanese Application No. 2010-507552, dated May 29, 2012.
Office Action for Japanese Application No. 2010-507552, dated Jan. 7, 2013.
Office Action for U.S. Appl. No. 12/114,498, mailed Sep. 16, 2011.
Office Action for U.S. Appl. No. 12/114,498, mailed Dec. 22, 2010.
International Preliminary Report on Patentability for PCT/US2008/062415, dated Nov. 12, 2009.

(56) References Cited

OTHER PUBLICATIONS

International Search Report and Written Opinion for International Application No. PCT/US2008/062415, mailed Oct. 13, 2008.
Ahn, et al., "Structure-Activity Relationships of Pyrroloquinazolines as Thrombin Receptor Antagonists," *Bioorg. Med. Chem. Lett.* 9:2073-2078, 1999.
Aihara, et al., "Glycoprotein Ib Has a Partial Role in Platelet-von Willebrand Factor Collagen Interaction," *Thromb Haemost.*, 60(2):182-187, 1988.
Andrade-Gordon et al., "Design, synthesis, and biological characterization of a peptide-mimetic antagonist for a tethered-ligand receptor," *PNAS*, 96(22):12257-12262, 1999.
Angiolillo, et al., "Functional Effects of High Clopidogrel Maintenance Dosing in Patients with Inadequate Platelet Inhibition on Standard Dose Treatment," *The American Journal of Cardiology Online*,www.AJConline.org, Dec. 17, 2007.
Behan, et al., "Inhibitory effects of $P2Y_{12}$ receptor antagonists on TRAP-induced platelet aggregation, procoagulant activity, microparticle formation and intracellular calcium respones in patients with acute coronary syndromes," *Platelets*, 16(2):73-80, 2005.
Bernatowicz, et al., "Development of Potent Thrombin Receptor Antagonist Peptides," *J. Med. Chem.*,39:4879-4887, 1996.
Boeynaems, et al., "Overview of the P2 Receptors," *Seminars in Thrombosis and Hemostatis*, 31:2, 2005.
Borman, "Hope Rides on Drug Candidates," *Chemical & Engineering*, 83(16):40-44, 2005.
Broughton et al., Radioimmunoassay of antibiotics and chemotherapeutic agents, *Clin. Chem.* 22:726-732, 1976.
Butler, "Drug Immunoassays," *J. Immunol. Meth.*, 7:1-24, 1975.
Bye, A., et al., "Effect of a single Oral Dose of Asprin on the Platelet Aggregation Response to Arachidonic Acid," *British Journal of Clinical Pharmacology*, 7:283-286, 1979.
Cannon, et al., "ACC Clinical Data Standards," *J. Am. Coll. Cardiol.*,38(7):2114-2130, Dec. 2001.
Cattaneo,"The P2 Receptors and Congenital Platelet Function Defects," *Seminars in Thrombosis and Hemostasis*, 31(2):168-173, 2005.
Chackalamannil, et al., "Thrombin receptor (PAR-1) antagonist as novel antithrombotic agents," *Expert Opin. ther. Patents*, 16(4):493-505 (2006).
Chackalamannil et al., Discovery of a novel, orally active Himbacine-based thrombin receptor antagonist (SCH 530348) with potent antiplatelet activity, *J. Med. Chem.*, 51:3061-3064, 2008.
Chackalamannil, "G-protein coupled receptor antagonists-1: protease activated receptor-1 (PAR-1) antagonists as novel cardiovascular therapeutic agents," *Current Topics in Medicinal Chemistry*, 3:1115-1123, 2003.
Chackalamannil et al., "Discovery of potent orally active thrombin receptor (protease Activated Receptor 1) antagonists as novel antithrombotic agents," *J. Med. Chem.*, 48:5884-5887, 2005.
Chibata, Ichiro "Immobilized Enzymes: Research and Development," *Halsted Press, New York 1978, Quarterly Rev Biol*, 54(3):321, 1979.
Clasby et al., "Discovery and synthesis of a novel series of quinoline-based thrombin receptor (PAR-1) antagonists," *Bioorganic & Medicinal Chemistry Letters*, 16:1544-1548, 2006.
Clasby et al., "Metabolism-based identification of a potent thrombin receptor antagonist," *J. Med. Chem.*, 50:129-138, 2007.
Clasby et al., "Himbacine derived thrombin receptor antagonists: discovery of a new tricyclic core," *Bioorganic & Medicinal Chemistry Letters*, 17:3647-3651, 2007.
Coller, Barry S., et al., "A Murine Monoclonal Antibody that Completely Blocks the Binding of Fibrinogen to Platelets Produces a Thrombasthenic-like State in Normal Platelets and Binds to GlycoproteinsIIb and/or IIIa," *Journal Clinical Investigation*, 72:325-338, 1983.
Coller et al., "Evidence that glycocalicin circulates in normal plasma," *J Clin Invest*, 73(3):794-9, 1984.
Coller et al., "Monoclonal antibodies to platelet glycoprotein IIb/IIa as antithrombotic agents" Progress in Vascular Biology Hemostasis, and Thrombosis, vol. 614, (Feb. 28, 1991) p. 193-213.
Coller et al., "Thrombin receptor activating peptides: importance of the N-terminal serine and its ionization state as judged by pH dependence, nuclear magnetic resonance spectroscopy, and cleavage by aminopeptidase M.," Biochemistry 1992 31:11713.
Coller et al., "Collagen-platelet interactions: evidence for a direct interaction of collagen with platelet GPIa/IIa and an indirect interaction with platelet GPIIb/IIIa mediated by adhesive proteins," *Blood*, 74(1):182-92.
Colman, R. W., "Hemostasis and Thrombosis: Basic Principles and Clinical Practice", Section 30, pp. 472-485, 1.sup.st Edition, Lippincott williams & Wilkins, 1982.
Cook, Nigel S., et al., "Platelet Glycoprotein IIb/IIIa Antagonists," *Drugs of the Future*, 19:135-159, 1994.
Coughlin, "How the protease thrombin talks to cells," *PNAS USA*,96:11023-11027, 1999.
Covic et al., "Biphasic Kinetics of Activation and Signalting for PAR1 and PAR4 Thrombin Receptors in Platelets," *Biochemistry*,39:5458-5467, 2000.
Covic et al., "Role of the PAR4 Thrombin Receptor in Stabilizing Platelet-platelet Aggregates as Revealed by a Patient with Hermansky-Pudlak Syndrome," *Thromb. Haemost.*,87:722-727, 2002.
Cuatrecasas, "Protein Purification by Affinity Chromatography," *The Journal of Biological Chemistry*, 245:3059-3065, 1970.
Cuisset et al., "Relation of Low Response to Clopidogrel Assessed With Point-of-Care Assay to Periprocedural Myonecrosis in Patients Undergoing Elective Coronary Stenting for Stable Angina Pectoris," *Am. J. Cardiol.*, 1700-1703, 2008.
Curtin, et al., "Clopidogrel and Ticlopidine," *Platelets*, 51:787-801, 2002.
Database Medline, database accession No. NLM11285593, 2001.
Demarco, et al., "Function of Glycoprotein Ibα in Platelet Activation Induced by α-Thrombin," *J. Biol. Chem*, 266:23776-23783, 1991.
Erin, A N et al., "Formation of Alpha Tocopherol Complexes with Fatty-Acids A Hypothetical Mechanism of Stabilization of Bio Membranes by Vitamin E," *Biochimica et Biophysica ACTA*, 774:96-102, 1984.
Fabian, et al., "Near-Infrared Absorbing Dyes," *Chem. Rev*, vol. 92:1197-1226, 1992.
Fox, et al., "Structure of the Glycoprotein Ib.IX Complex from Platelet Membranes", *J. Biol. Chem.*. 263:4882-4890, 1988.
Fox et al., "Inhibition of ADP-induced intracellular $Ca_2$ responses and platelet aggregation by the $P2Y_{12}$ receptor antagonists AR-C69931MX and clopidogrel is enhanced by prostaglandin El ," *Cell Calcium*,35:39-46, 2004.
Gachet et al., "The Platelet P2 Receptors in Thrombosis," *Seminars in Thrombosis and Hemostasis*, 31(2):162-167, 2005.
Galfre et al., "Preparation of monoclonal antibodies: strategies and procedures," *Methods of Enzymology* 73(Pt B):3-46, 1981.
Geiger et al., "Thrombosis-Specific Impairment of Human Platelet $P2Y_{AC}$ADP Receptor-Mediated Signaling by the Antiplatelet Drug Clopidogrel," *Arteriosclerosis, Thrombosis, and Vascular Biology*, 19:2007-2011, 1999.
Gurbel et al., "Platelet Function Monitoring in Patients With Coronary Artery Disease," *Journal of the American College of Cardiology*, 50(19):1822-1834, 2007.
Hechler et al., "The P2 Receptors in Platelet Function," *Seminars in Thrombosis and Hemostasis*, 31(2):150-161, 2005.
Hoekstra et al., "thrombin Receptor (Par-1) Antagonists. Heterocycle-Based Peptidomimetics of the SFLLr Agonist Motif," *Bioorg. Med. Chem. Lett.*,8:1649-1654, 1998.
Hui, et al., "Minimal Sequence Requirement of Thrombin Receptor Agaonist Peptide," *Biochem. Biophys. Res Commun.*, 184:790, 1992.
Hung et al., "The Cloned Platelet Thrombin Receptor Couples to at Least Two Distinct Effectors to Stimulate Phosphoinositide Hydrolysis and Inhibit Adenylyl Cyclase," *J. Biol. Chem.*, 267:20831-20834, 1992.

(56) References Cited

OTHER PUBLICATIONS

Hung et al., "Cloned Platelet Thrombin Receptor is Necessary for Thrombin-induced Platelet Activation," *J. Clin. Invest.*, 89:1350-1353, 1992.

Iakovou et al., "Incidence, predictors, and outcome of thrombosis after successful implantation of drug-eluting stents," *JAMA*, 293(17):2126-2130, 2005.

Ikeda et al., "Cilostazol," *Platelets*, 53:817-823, 2002.

Ingerman et al., "Hereditary Abnormality of Platelet Aggregation Attributable to Nucleotide Storage Pool Deficiency", *Blood*, 52:2, 1978.

Jacobson et al., "Molecular Recognition at Adenine Nucleotide (P2) Receptors in Platelets," *Seminars in Thrombosis and Hemostasis*, 31(2):205-216, 2005.

Jakubowski et al., "the use of the VerifyNow P2Y12 point-of-care device to monitor platelet function across a range of P2Y12 inhibition levels following prasugrel and clopidogrel administration," *Thromb. Haemost.*,99:409-415, 2008.

Jarvis et al., "ADP can induce aggregation of human platelets via both $P2Y_1$ and $P_{2T}$ receptors," *British Journal of Pharmacology*,129:275-282, 2000.

Kahn et al., "Protease-activated receptors 1 and 4 mediate activation of human platelets by thrombin," *J. Clin. Invest.*,103:879-887, 1999.

Kahn et al., "A dual thrombin receptor system for platelet activation," *Nature*,394:690-694, 1998.

Kai et al., "Prevention of the Hypercontractile Response to Thrombin by Proteinase-Activated Receptor-1 Antagonist in Subarachnoid Hemorrhage," *Stroke*, 38(12):3259-3265, 2007.

Kim et al., "Cilostazol Could Ameliorate Platelet Responsiveness to Clopidogrel in Patients Undergoing Primary Percutaneous Coronary Intervention," *Circ. J.*,71:1867-1872, 2007.

Kohler et al., "Continuous cultures of fused cells secreting antibody of predefined specificity," *Nature*, 256:495-497, 1975.

Kogushi, et al., "[P-M-059] Effects of E5555, A Protease-Activated Receptor-1 Antagonist, on the Inflammatory Markers in Vitro," *J. Thromb. Haemost.*, 5:Suppl. 2:P-M-059, 2007.

Kowalska, et al., "Alboaggregins A and B. Structure and Interaction with Human Platelets", *Thromb Haemost*, 79:609-613, 1998.

MacFarlane et al., "Proteinase-Activated Receptors," *Pharmacol. Rev.*, 53:245-282., 2001.

Marcucci et al., "Cardiovascular Death and Nonfatal Myocardial Infarction in Acute Coronary Syndrome Patients Receiving Coronary Stenting Are Predicted by Residual Platelet Reactivity to ADP Detected by a Point-of-Care Assay. A 12-Month Follow-Up," *Circulation J Am Heart Assoc*, 119: 237-242, 2009.

Marcus et al., "Role of CD39 (NTPDase-1) in Thromboregulation, Cerebroprotection, and Cardioprotection," *Seminars in Thrombosis and Hemostasis*, 31(2):234-246, 2005.

Maryanoff et al., Discovery of Potent Peptide-Mimetic Antagonists for the Human Thrombin Receptor, Protease-Activated Receptor-1 (PAR-1), *Curr. Med. Chem. Cardiovasc. Hematol. Agents*, 1(1):13-36, 2003.

Mauri, et al., "Stent thrombosis in randomized clinical trials of drug-eluting stents," *N. Engl. J. Med.*, 356:1020-1029, 2007.

McComsey et al., "Macrocyclic Hexapeptide Analogues of the Thrombin Receptor (PAR-1) Activation Motif SFLLRN," *Bioorg. Med. Chem. Lett.*, 9:255-260, 1999.

McLean and Cannon, "The Clinical Potential of a Point-of-Care Assay to Assess Interindividual Variability in Platelet Aggregation Among Patients Taking Clopidogrel," *Critical Pathways in Cardiology*,5:103-113, 2006.

McLean and Cannon, "A point-of-care assay to measure platelet aggregation in patients taking clopidogrel," *Future Cardiol.*, 2:255-267, 2006.

Michelson, "Flow Cytometry: A Clinical Test of Platelet Function" Blood (Jun. 15, 1996) 87:4925-4936.

Meinke, et al., "Empirical model functions to calculate hematocrit-dependentoptical properties of human blood," *Applied Optics*, 46(10):1742-1753, 2007.

Minamoto et al., "Detection of Platelet Adhesion/Aggregation to Immobilized Ligands on Microbeads by an Aggregometer", *Thrombosis and Hemostasis*, 76(6):1072-9, 1996.

Moncada et al., "Arahidonic Acid Metabolites and the Interactions between Platelets and Blood-Vessel Walls", *The New England Journal of Medicine*, 300(20):1142-1147, 1979.

Muller et al., "Prevalence of Clopidogrel Non-Responders Among Patients with Stable Angina Pectoris Scheduled for Elective Coronary Stent Placement," *Thrombosis and Haemostasis* 89(5):783-787, 2003.

Nessel, "On "Current Role of Antithrombotic Agents in the Treatment of Actue Coronary Syndromes,"" *Seminars in Thrombosis and Hemostasis*, 31(2):248, 2005.

Niitsu et al., "Pharmacology of CS-747(Prasugrel, LY640315), a Novel, Potent Antiplatelet Agent with in Vivo $P2Y_{12}$ Receptor Antagonist Activity," *Seminars in Thrombosis and Hemostasis*, 1(2):184-194, 2005.

O'Donnell et al., "Antiplatelet Therapy for Secondary Prevention of Noncardioembolic Ischemic Stroke," *Stroke*, 39:1638-1646, 2008.

Okita et al., "On the association of glycoprotein Ib and actin-binding protein in human platelets," *J. Cell Biol.*, 100(1):317-321, 1985.

Packham et al., "Platelet Aggregation and Adenosine Diphosphate/Adenosine Triphosphate Receptors: A Historical Perspective," *Seminars in Thrombosis and Hemostasis*, 31(2):129-138, 2005.

Packham, "Platelet Function Inhibitors," *Thrombosis and Haemostasis*, 50(2):610-619, 1983.

Patti et al.,"Point-of-Care Measurement of Clopidogrel Responsiveness Predicts Clinical Outcome in Patients Undergoing Percutaneous Coronary Intervention," *Journal of the American College of Cardiology*, 52(14):1128-1133, 2008.

Playfair et al., "Production of antibodies and binding reagents," *Br. Med. Bull.*, 30: 24-31, 1974.

Price et al., "Prognostic significance of post-clopidogrel platelet reactivity assessed by a point-of-care assay on thrombotic events after drug-eluting stent implantation," *European Heart Journal* 29:992-1000,2008.

Rao Gundu et al., "Antioxidants, atherosclerosis and thrombosis" *Prostaglandins Leukotrienes and Essential Fatty Acids*,54(3):155-166, 1996.

Robson et al., "Ectonucleotidases of CD39 Family Modulate Vascular Inflammation and Thrombosis in Transplantation," *Seminars in Thrombosis and Hemostasis*, 31(2):217-233, 2005.

Ruan et al., "Studies of a Monoclonal Antibody (SZ-51) Specific for an Alpha-Granule Membrane Protein (GMP-140)," *Thrombosis Research*, 63(2):280, Jul. 1991.

Ruan, et al., "Monoclonal Antibody to Human Platelet Glycoprotein I: II. Effects on Human Platelet Function" *British Journal of Haematology*, 49:501-509 and 511-519, 1981.

Sabo et al., "Structure-activity studies of the thrombin receptor activating peptide," *Biochem. Biophys. Res. Commun.*,188: 604, 1992.

Savi et al., "Clopidogrel and Ticlopidine: P2Y12 Adenosine Diphosphate-Receptor Antagonists for the Prevention of Atherothrombosis," *Seminars in Thrombosis and Hemostasis*, 31:174-183, 2005.

Scarborough et al., "Tethered ligand agonist peptides. Structural requirements for thrombin receptor activation reveal mechanism of proteolytic unmasking of agonist function," *J. Biol. Chem.*, 267:13146, 1992.

Scudder et al., "Preparation and functional characterization of monoclonal antibodies against glycoprotein Ib," *Methods in Enzymology*, 215:295-311, 1992.

Smith et al., "Rapid Platelet-Function Assay," *Journal of the American Heart Assoc., Circulation*, 99:620-625, 1999.

Smyth and Fitzgerald, "Human Prostacyclin Receptor," *Vitamins and Hormones*,65:149-165, 2002.

Soslau et al., "Unique Patthway of Thrombin-induced Platelet Aggregation Mediated by Glycoprotein Ib," *J. Biol. Chem.* ,276(24):21173-21183, 2001.

Steinhubl et al; "Point-of-Care Measured Platelet Inhibition Correlates With a Reduced Risk of an Odverse Cardiac Event after Percutaneous Coronary Intervention," *Circulation Journal of the American heart Association*, 103:2572-2578, 2001.

(56) References Cited

OTHER PUBLICATIONS

Stejskal et al., "Application of Cationic Propyl Gallate as Inducer of Thrombocyte Aggregation for Evaluation of Effectiveness of Antiaggregation Therapy," *Biomedical Papers,* 145(2):69-74, 2001.
Storey et al., "Inhibition of ADP-induced P-selection Expression and Platelet-Leukocyte Confugate Formation," *Thromb. Haemost.,* 88(3):488-494, 2002.
Storey et al., "Potentiation of platelet aggregation by heparin in human whole blood is attentuated by P2Y12 and P2Y1 antagonists but not aspirin," *Thromb. Res.,*115(4):301-307, 2005.
Tanaka, et al., "Flow cytometric platelet enumeration utilizing monoclonal antibody CD42a," *Clin. Lab Haematol.,* 18:265-269, 1996.
The EPIC Investigators, "Use of a Monoclonal Antibody Directed Against the Platelet Blycoprotein IIb/IIIa Receptor in High-Risk Coronary Angioplasty," *New England Journal of Medicine,* 330:956-961, 1994.
Van Giezen and Humphries, "Preclinical and Clinical Studies with Selective Reversible Direct P2Y12 Antagonists," *Seminars in Thrombosis and Hemostasis,* 31(2):195-204, 2005.
Varenhorst et al., "Assessment of PsY12 inhibition with the point-of-care device VerifyNow TM P2Y12 in patients treated with prasugrel or clopidogrel co-administered with asprin," manuscript submitted Apr. 29, 2008 to the European Heart Journal.
Vassallo et al., "Structure-Function Relationships in the Activation of Platelet Thrombin Receptors by Receptor-derived Peptides," *Biol. Chem.,* 267:6081-6085, 1992.
Vu et al., "Molecular Cloning of a Functional Thrombin Receptor Reveals a Novel Proteolytic Mechanism of Receptor Activation," *Cell,* 64:1057-1068, 1991.
Vu et al., "Domains specifying thrombin-receptor interaction," *Nature,* 353:674-677, 1991.
Wade, Hybridomas: a potent new biotechnology, *Science,* vol. 208 p. 692, 1980.
Walenga and Hoppenstead, "Monitoring the New Antithrombotic Drugs," *Seminars in Thrombosis and Hemostasis,* 31(2):247, 2005.
Wang et al., "Prostaglandine1 and Dibutryl Cyclic Amp Enhance Platelet Resistance to Deformation," *Thrombosis Research,* 65(6):757-768, 1992.
Ward, et al., "Mocarhagin, a Novel Cobra Venom Metalloproteinase, Cleaves the Platelet von Willebrand Factor Receptor Glycoprotein Ibα as a Binding Site for von Willebrand Factor and α-Thrombin," *Biochemistry,*35: 4929-4938, 1996.
Welsh, "Antibody production made easier," *Nature,* 266:495, 1977.
Xu et al., "Cloning and characterization of human protease-activated receptor 4," *PNAS USA,* A229:6642-6646, 1998.
Office Action for U.S. Appl. No. 10/886,155, mailed Aug. 1, 2005.
Office Action for U.S. Appl. No. 10/886,155, mailed Mar. 7, 2006.
Office Action for Chinese Application No. 200880022878.8, dated Apr. 18, 2013.
Office Action for Japanese Application No. 2010-506656, dated Aug. 13, 2013.
Office Action for European Application No. 06769917, mailed Jun. 18, 2009.
Office Action for Indian Patent Application No. 7901/DELNP/2007, dated Mar. 12, 2013.
Office Action for Korean Application No. 10-2013-7005263, dated Apr. 25, 2013.
Office Action for Indian Patent Application No. 7932/DELNP/2007, dated Apr. 10, 2013.
Office Action for Japanese Application No. 2008-508905 dated Jan. 7, 2013.
Office Action for Korean Application No. 10-2007-7027636, dated Jun. 27, 2013.
Michelson, A. D. et al., "Current options in platelet function testing," Am. J. Cardiol., 2006, 98:4N-10N.
Coller et al. (1993). "Studies of activated GPIIb/IIIa receptors on the luminal surface of adherent platelets. Paradoxical loss of luminal receptors when platelets adhere to high density fibrinogen," *J Clin Invest,* 92(6): 2796-2806.
Coller, (1980). "Interaction of Normal, Thrombasthenic, and Bernard-Soulier Platelets with Immobilized Fibrinogen: Defective Platelet-Fibrinogen Interaction in Thrombasthenia," *Blood,* 55(2):169-178.
Marcus, (1982). "Platelet Lipds," in *Haemostasis and Thrombosis:* Basic Principles and Clinical Practice, Chapter 30, Section D. Platelet Function and its Disorders, Colman, R. W. et al. (eds.), pp. 472-485.
Ruan et al. (1986). "Monoclonal Antibodies and Human Blood Platelets," *INSERM Symposium,* 27:59-68.
Shim et al. (2008). "The clopidogrel resistance can be attenuated with triple antiplatelet therapy in patients undergoing drug-eluting stents implantation," *International Journal of Cardiology,* doi:10.1016/j.ijcard, 5 pages.
URL, R&D, http://www.eisai.co.jp/pdf/ir/mat/material20050830.pdf, (2005).
Varenhorst, C. et al. (2008). "Assessment of the platelet inhibitory effects of clopidogrel and prasugrel by the VerifyNow P2Y12 point-of-care device in comparison with LTA and VASP-phosphorylation in aspirin treated CAD patients," European Heart Journal, Abstract P2597, 29 (Abstract Supplement):404.
Office Action for Chinese Application No. 200880022878.8, dated Jan. 8, 2014.
Office Action for Japanese Application No. 2010-506656, dated Apr. 22, 2014.
Notice of Preliminary Rejection for Korean Application No. 10-2009-7024975, issued Oct. 14, 2014.
Office Action for U.S. Appl. No. 12/943,413, mailed Jun. 9, 2014.
Office Action for U.S. Appl. No. 12/943,413, mailed Mar. 16, 2015.
Office Action for U.S. Appl. No. 14/031,926, mailed Dec. 3, 2015.
Office Action for Indian Patent Application No. 7901/DELNP/2007, dated Mar. 4, 2014.
Notice of Last Preliminary Rejection for Korean Application No. 10-2013-7005263, dated Jan. 29, 2014.
Notice of Preliminary Objection for Korean Application No. 10-2015-7004839, dated Apr. 25, 2015.
Office Action for Canadian Patent Application No. 2,604,845, dated Jul. 31, 2012.
Office Action for Indian Patent Application No. 7932/DELNP/2007, dated Jan. 24, 2014.
Notice of Preliminary Rejection for Korean Application No. 10-2009-7025187, dated Oct. 27, 2014.
Anders, R. et al., "Xemilofiban Orbofiban: Insight into Drug Development," Cardiovascular Drug Reviews, 19(2):116-132 (2001).
Kreutz, R. P. et al., "Inhibition of platelet aggregation by prostaglandin E1 (PGE1) in diabetic patients during therapy with clopidogrel and aspirin," Platelets, 24(2):145-150 (2013).
Sangkuhl, K. et al., "Platelet aggregation pathway," Pharmacogenet Genomics, 21(8):516-521 (Aug. 2011).
Springthorpe, B. et al., "From ATP to AZD6140: The discovery of an orally active reversible P2Y12 receptor antagonist for the prevention of thrombosis," Bioorg. Med. Chem. Lett., 17:6013-6018 (2007).

* cited by examiner

METHODS FOR MEASURING PLATELET REACTIVITY OF INDIVIDUALS TREATED WITH DRUG ELUTING STENTS

CROSS-REFERENCE TO RELATED APPLICATIONS

This application is the national stage entry of PCT/US2008/62297, filed May 1, 2008, which is a continuation of U.S. application Ser. No. 11/742,684, filed May 1, 2007, now abandoned. All of the above applications are fully incorporated herein by reference.

FIELD OF THE INVENTION

This invention relates to the field of diagnostic assays, and in particular to methods and kits for measuring platelet reactivity of individuals treated with drug-eluting stents (DES).

BACKGROUND OF THE INVENTION

The role of platelets in mammalian physiology is extraordinarily diverse, but their primary role is in promoting hemostasis. In many situations, an evaluation of the ability of blood to clot is desired, a parameter that is frequently controlled by the ability of platelets to adhere and/or aggregate. Of interest, therefore, is the assessment of the adhesive functions of platelets. For example, questions of interest include whether to administer drugs that will block, or promote, clot formation, or whether to detect deficiencies in platelet function prior to surgical procedures. Also of interest is evaluating the effectiveness of a platelet inhibitor that is being tested as a new drug or is being used as approved clinical treatment in a patient.

Platelets are known to aggregate under a variety of conditions and in the presence of a number of different reagents. Platelet aggregation is a term used to describe the binding of platelets to one another. Platelet aggregation in vitro depends upon the ability of platelets to bind fibrinogen to their surfaces after activation by an aggregation-inducing agent such as thrombin, ADP or collagen.

Platelets play a critical role in the maintenance of normal hemostasis. When exposed to a damaged blood vessel, platelets will adhere to exposed sub-endothelial matrix. Following the initial adhesion, various factors released or produced at the site of injury such as thrombin, thrombin, ADP and collagen activate the platelets. Once platelets are activated, a conformational change occurs in the platelet glycoprotein GPIIb/IIIa receptor, allowing it to bind fibrinogen and/or von Willebrand factor.

It is this binding of the multivalent fibrinogen and/or von Willebrand factor molecules by GPIIb/IIIa receptors on adjacent platelets that results in the recruitment of additional platelets to the site of injury and their aggregation to form a hemostatic plug or thrombus.

In vitro platelet aggregometry is the laboratory method used to assess the in vivo ability of platelets to form the aggregates leading to a primary hemostatic plug. In this technique an aggregating agent such as thrombin, ADP or collagen is added to whole blood or platelet-rich plasma and aggregation of platelets monitored. Platelet aggregometry is a diagnostic tool that can aide in patient diagnosis and selection of therapy. Current assays to measure platelet aggregation are expensive, time-consuming, cumbersome, and generally not suitable for a clinical environment.

A rapid platelet function assay has been developed and is described in U.S. Pat. No. 5,763,199 (Coller). The assay determines glycoprotein GPIIb/IIIa receptor blockade in whole blood. Agglutination of small polymeric beads coated with a GPIIb/IIIa ligand such as fibrinogen results when the beads are contacted with whole blood containing platelets with activated GPIIb/IIIa receptors that are not blocked. Failure to agglutinate indicates either failure of the GPIIb/IIIa receptors to become activated and/or blockade of the GPIIb/IIIa receptors. In a preferred embodiment, the addition of a thrombin receptor activator results in an assay that is rapid and convenient enough to be performed at the bedside and that results in agglutination of the small polymeric beads within a convenient, known period of time if the GPIIb/IIIa receptors are not blocked. The assay includes the ability to transfer blood to be tested from a collection container to an assay device without opening the collection container. This platelet aggregation assay can be conducted at the same time as the activated clotting time (ACT), which is performed to assess the adequacy of heparinization.

Platelet aggregation plays a key role in the pathogenesis of thrombosis and acute coronary artery disease. Evidence suggests that significant platelet function variability exists in the response to various antiplatelet agents. It has also been demonstrated that an inter-individual variability in platelet aggregation exists when P2Y12 antagonists such as clopidogrel are used for treatment of patients to achieve an anti-aggregation effect. The results of one study demonstrated that at least 10% of patients receiving the drug did not achieve the expected platelet aggregation inhibition (Muller, et al., *Thromb. Haemost.* (2003) 89(5):783-787).

Clopidogel and ticlopidine are thienopyridine derivatives that inhibit platelet aggregation. They are believed to inhibit the binding of adenosine-5-diphosphate (ADP) to one of its receptors, the P2Y12 receptor. The pharmacological activity of clopidogrel is very similar to the pharmacological activity of ticlopidine. However, clopidogrel has been shown to have fewer side-effects than ticlopidine. Based on mounting evidence of the efficacy of clopidogrel in thrombotic disease, the use of clopidogrel and other P2Y12 antagonists are likely to increase significantly.

Since many patients with cardiovascular disease are currently taking one of the thienopyridine agents, a method for detection of resistance to a thienopyridine and assessment of the efficacy of thienopyridine treatment would be beneficial. Thus, there is a need to develop an assay that would provide information about aspirin and thienopyridine, e.g., clopidogrel or ticlopidine, sensitivity and efficacy of treatment in a given patient.

The effects of these agents on platelet function have been assessed with platelet aggregometry using ADP, collagen or other platelet activators. However, since ADP activates at least two different receptors (P2Y1 and P2Y12 and perhaps P2X1), it has the potential for lower specificity and background noise. Collagen is another choice. However collagen is highly variable due its quaternary structure, which dramatically affects it ability to activate platelets and due to the fact it is derived from biological tissue and sensitive to minor changes in temperature and pH. Neither collagen nor ADP provide specificity to the P2Y12 receptor and therefore by themselves are not the optimal choice for the determination of the effects of P2Y12 inhibitors. In particular as has been shown in several studies, the choice of concentration of these two agonists has significant effect on the degree of inhibition to P2Y12 antagonists that is measured.

Prostaglandins (PGs) belong to a ubiquitous class of chemicals known as eicosanoids. They are found in virtually every tissue in the body and have a very wide spectrum of biological activities. Eicosanoids are derivatives of arachidonic acid, a polyunsaturated fatty acid. The term eicosanoids includes the family of prostaglandins (PGs); prostacyclin, thromboxanes, and leukotrienes. The PGs are divided in different families depending on their structure, each designated by a letter (A, E, F, G, H, or I). In addition to this letter, each individual prostaglandin carries a digit that indicates the number of double bonds in its fatty acid side chain. For example, prostaglandin E1 (PGE1) belongs to the E family and has only one double bond in its side chain. PGs play an important role in platelet aggregation and hemostasis (blood clotting) and typically have a marked vasodilator effect.

PGE1 is the theoretical cyclooxygenase metabolite of dihomo-γ-linolenic acid (DGLA), but it is virtually undetectable in the plasma of normal humans or other animals. Its pharmacology includes vasodilation, hypotension, and antiplatelet activities. PGE1 has been shown to inhibit platelet aggregation by increasing cyclic adenosine monophosphate (CAMP) concentrations within platelets. A number of groups have shown that the IC50 of PGE1 for the inhibition of ADP-induced human platelet aggregation is around 40 nM.

Platelet reactivity studies have demonstrated a wide interindividual variability in the inhibitory response to clopidogrel. Retrospective and small prospective studies have demonstrated an association between a poor response to clopidogrel and clinical events after percutaneous coronary intervention (PCI). Separate from the reduction in aggregation caused by clopidogrel as judged by the percentage reduction in response to ADP, the absolute value of post-clopidogrel platelet aggregation (i.e., post-treatment reactivity), may be an adequate measure of the risk of subsequent events. From a clinical perspective, the routine measurement of platelet reactivity at the time of PCI is generally impractical because of the need to use specialized laboratory techniques such as light transmittance aggregometry (LTA).

A drug-eluting stent (DES) is a metal scaffold placed into a narrowed, diseased coronary artery that gradually releases medication directly to the arterial wall in order to block cell proliferation. As currently used in clinical practice, the term "drug-eluting stents" refers to metal stents which elute a drug designed to limit the growth of neointimal scar tissue, thus reducing the likelihood of restenosis, i.e., blockade of the stented artery. Drug-eluting stents in current clinical use have been shown to be statistically superior to bare-metal stents (BMS) for the treatment of native coronary artery narrowing, having lower rates of major adverse cardiac events, defined as a composite clinical endpoint of death, myocardial infarction and repeat intervention necessitated by restenosis.

Though less frequent with drug-eluting stents, neointimal proliferation can still occur with DES and cause restenosis. For example, stent occlusion due to thrombosis ("stent thrombosis") may occur during the procedure, in the days immediately following the procedure, or later. Treatment with antithrombotic agents such aspirin and clopidogrel appears to reduce the risk of thrombosis, and early cessation of one or both of these drugs after drug-eluting stenting has been shown to markedly increase the risk of stent thrombosis and myocardial infarction (Iakovou, et al., *JAMA* (2005) 293(17):2126-2130).

As described above, there is a wide variability among different individuals in the platelet inhibitory response to antithrombotic agents such as clopidogrel. Thus, there is a compelling need to provide methods for measuring platelet reactivity of individuals treated with drug-eluting stents (DES).

SUMMARY OF THE INVENTION

It is an object of the present invention to provide methods for measuring platelet reactivity of individuals treated with drug-eluting stents (DES).

Another object of the present invention is to provide methods for identifying individuals treated with DES who are at risk for stent thrombosis.

Yet another object of the invention is to provide methods for measuring clopidogrel-induced inhibition of platelet reactivity in individuals treated with DES.

These and other objects of the present invention are achieved in a method of measuring platelet reactivity of an individual treated with a DES. First, a blood sample is obtained from an individual treated with a DES and a P2Y12 antagonist. The blood sample is then mixed with particles comprising an attached GPIIb/IIIa receptor ligand, adenosine diphosphate (ADP) and prostaglandin E1 (PGE1). The mixture is incubated under conditions suitable for agglutinating particles, and platelet-mediated agglutination is assessed in the mixture. The absence or reduction of agglutination indicates that the individual treated with the DES and the P2Y12 antagonist has reduced platelet reactivity.

In another embodiment, an alternative method is provided of measuring platelet reactivity of a PCI patient that has a (DES). A blood sample is obtained from the patient. The blood sample is mixed in combination with 1) an anticoagulant; 2) sufficient buffer to maintain the pH and salt concentration of the anticoagulated blood within a range suitable for platelet aggregation; 3) a platelet GPIIb/IIIa receptor ligand immobilized on a solid surface; 4) one or more agents to enhance a signal transduction pathway and 5) a receptor activator. The combination is incubated under conditions for agglutinating particles. Platelet-mediated agglutination is assessed in the mixture. The absence of agglutination indicates that the patient has reduced ability to form platelet thrombi.

In yet another embodiment, a method is provided for measuring platelet reactivity of a patient that has a (DES). An ADP platelet activator is added to a blood sample obtained from the patient. One or more platelet inhibitors are provided to the sample. At least one of the platelet inhibitors is Prostaglandin E1 (PGE1). An alternate signal transduction pathway is produced in response to providing an ADP platelet activator and one or more platelet inhibitors. In response to producing the alternate signal transduction pathway, a final concentration of ADP is about 2 to 35 µM and a final concentration of PGE1 is about 2 to 30 nM. Platelet reactivity of the patient is measured in response to the final concentration of the ADP.

In one embodiment of the present invention, a method is provided for identifying an individual treated with a DES at risk for stent thrombosis. First, a blood sample is obtained from an individual treated with a DES and a P2Y12 antagonist. The blood sample is then mixed with particles comprising an attached GPIIb/IIIa receptor ligand, adenosine diphosphate (ADP) and prostaglandin E1 (PGE1). The mixture is incubated under conditions suitable for agglutinating particles, and platelet-mediated agglutination is assessed in the mixture. The absence or reduction of agglutination indicates that the individual treated with the DES and the P2Y12 antagonist has reduced platelet reactivity. Based on the level of platelet reactivity, an assessment is made of a risk level of the individual for stent thrombosis.

In another embodiment, an alternative method is provided for identifying a patient with DES at risk for stent thrombosis. A blood sample is obtained from the patient. The blood sample is mixed in combination with 1) an anticoagulant; 2) sufficient buffer to maintain the pH and salt concentration of the anticoagulated blood within a range suitable for platelet aggregation; 3) a platelet GPIIb/IIIa receptor ligand immobilized on a solid surface; 4) one or more agents to enhance a signal transduction pathway and 5) a receptor activator. The combination is incubated under conditions for agglutinating particles. The absence of agglutination indicates that the patient has reduced ability to form platelet thrombi. Platelet reactivity of the patient is measure. In response to the measurement a determination is made of a risk level of the patient for stent thrombosis.

In one embodiment of the present invention, a method is provided for measuring clopidogrel-induced inhibition of platelet reactivity in individuals treated with DES. First, a blood sample is obtained from an individual treated with a DES and clopidogrel. The blood sample is then mixed with particles comprising an attached GPIIb/IIIa receptor ligand, adenosine diphosphate (ADP) and prostaglandin E1 (PGE1). The mixture is incubated under conditions suitable for agglutinating particles, and platelet-mediated agglutination is assessed in the mixture. The absence or reduction of agglutination indicates that the individual treated with the DES and clopidogrel has reduced platelet reactivity.

In another embodiment, an alternative method is provided for determining if a patient has clopidogrel-induced platelet inhibition. A blood sample is obtained from the patient. The blood sample is mixed in combination with 1) an anticoagulant; 2) sufficient buffer to maintain the pH and salt concentration of the anticoagulated blood within a range suitable for platelet aggregation; 3) a platelet GPIIb/IIIa receptor ligand immobilized on a solid surface; 4) one or more agents to enhance a signal transduction pathway and 5) a receptor activator. The combination is incubated under conditions for agglutinating particles. The combination is incubated under conditions for agglutinating particles. Platelet-mediated agglutination is assessed in the mixture. The absence of agglutination indicates that the patient has reduced ability to form platelet thrombi. Platelet reactivity of the patient is measured. A determining is then made to determine if the patient has clopidogrel-induced platelet inhibition.

In one embodiment of the present invention, a kit is provided for measuring inhibition of platelet aggregation by a P2Y12 receptor antagonist that includes a GPIIb/IIIa receptor ligand immobilized on a particle, adenosine diphosphate (ADP) and prostaglandin E1 (PGE1). In another embodiment, an anticoagulant and a buffer to maintain the anticoagulated blood in a condition suitable for platelet aggregation are also provided.

DETAILED DESCRIPTION OF THE INVENTION

Figure 1:
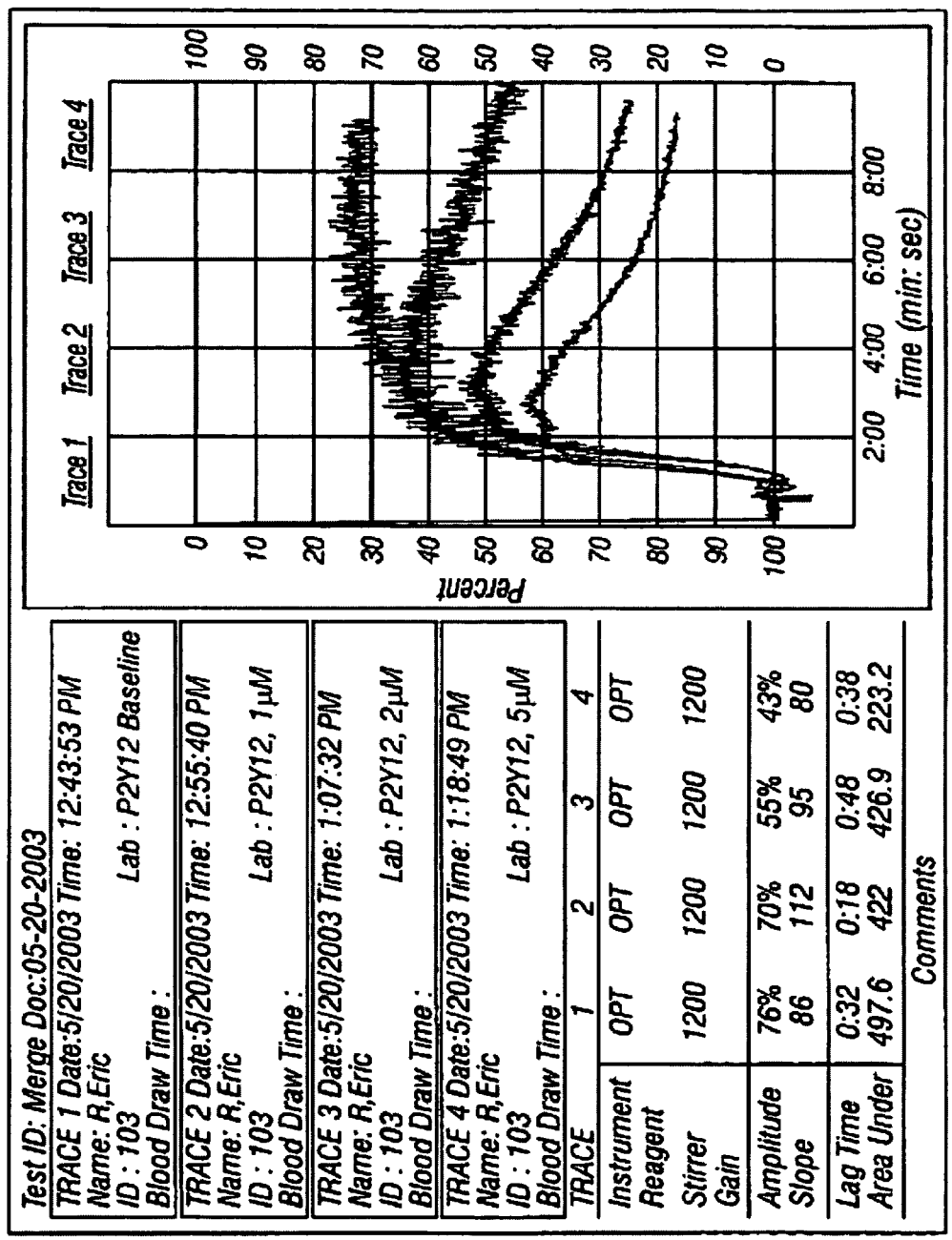
FIG. 1 illustrates the extent of platelet aggregation from a blood sample treated with a P2Y12 receptor antagonist, as measured by the assay of the present invention.

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entirety. If a definition set forth in this section is contrary to or otherwise inconsistent with a definition set forth in the patents, applications, published applications and other publications that are incorporated herein by reference, the definition set forth in this section prevails over the definition that is incorporated herein by reference.

Citation of publications or documents is not intended as an admission that any of such publications or documents are pertinent prior art, nor does it constitute any admission as to the contents or date of these publications or documents.

As used herein, "a" or "an" means "at least one" or "one or more."

As used herein, the term "individual" is not limited to a specific species or sample type. For example, the term "individual" may refer to a patient, and frequently a human patient. However, this term is not limited to humans and thus encompasses a variety of mammalian species.

As used herein, "treatment" means any manner in which the symptoms of a condition, disorder or disease are ameliorated or otherwise beneficially altered. Treatment also encompasses any pharmaceutical use of the compositions herein.

As used herein, the term "assessing" refers to any form of measurement, and includes determining if an element is present or not. The terms "assessing", "determining", "measuring", "evaluating", and "assaying" are used interchangeably and include both quantitative and qualitative determinations. Thus, the term "assessing" encompasses both determining the amount of something present, and determining whether it is present or not.

As used herein, the term "platelet reactivity" refers to platelet activation in response to injury and/or chemical stimuli. Platelet aggregation is the most common measure of platelet reactivity. Thus, the term "platelet reactivity" as used herein broadly refers to platelet aggregation in response to platelet activators such as, for example, ADP, thrombin, collagen or the like.

As used herein, the term "drug-eluting stent" or "DES" refers to a stent (i.e., expandable scaffold), usually made out of metal or a composite material, that is coated with a pharmaceutical agent known to interfere with the process of restenosis (re-blocking of the artery). This term is not limited to any particular drug-eluting stent. It encompasses, for example, the CYPHER™ sirolimus-eluting stent (Cordis), the TAXUS™ paclitaxel-eluting stent (Boston Scientific), the ENDEAVOR™ ABT-578-eluting stent (Medtronic), the XIENCE™ everolimus-eluting stent (Abbott), and the like.

As used herein, the term "stent thrombosis" is defined as proposed by the Academic Research Consortium (ARC)

(Mauri, et al., *N Engl. J. Med.* (2007) 356:1020-1029). The ARC definition includes patients with "definite," "probable" and "possible" thrombosis. Stent thrombosis is defined as "definite" when confirmed by angiography or when pathologic confirmation of acute thrombosis is made. "Probable" stent thrombosis is defined as any unexplained death within 30 days or as target vessel myocardial infarction (MI) without angiographic confirmation of thrombosis. "Possible" stent thrombosis is defined as unexplained death after 30 days. As used herein, "acute" stent thrombosis refers to stent thrombosis occurring within 24 hours of the percutaneous coronary intervention (PCI); "subacute" stent thrombosis refers to stent thrombosis occurring between 1 and 30 days after the PCI; and "late" stent thrombosis refers to stent thrombosis occurring later than 30 days after PCI.

As described above, in one embodiment of the present invention, methods are provided for measuring platelet reactivity of individuals treated with DES. In another embodiment, methods are provided for identifying those individuals treated with DES who are at risk for stent thrombosis. In yet another embodiment, methods are provided for measuring clopidogrel-induced platelet inhibition in individuals treated with DES.

In various embodiments of the present invention, a composition of ADP and PGE1 is utilized as an activator in measuring inhibition of platelet aggregation by P2Y12 antagonists such as thienopyridines in whole blood samples. Accordingly, the aforementioned compositions may be employed to determine the effectiveness of anti-platelet therapy involving treatment of patients with a thienopyridine. The above compositions may be employed in conjunction with particles coated with a GPIIb/IIIa receptor ligand and any other reagents necessary for conducting an assay for the efficacy of thienopyridines. A lyophilized reagent composition may be used that comprises the aforementioned activator composition and particles. In one approach, a metered volume of a sample to be measured such as whole blood is mechanically mixed with the lyophilized reagent. A change in light transmission is monitored and an index of platelet activity is calculated. In one aspect a whole blood sample is combined in a cuvette or a unitized cartridge with the aforementioned lyophilized reagent. An apparatus may be employed for carrying out the assay. The apparatus comprises a well for receiving the sample where the well contains the lyophilized reagent and other reagents for conducting the assay. The additional reagents may be various buffers and/or lyophilization stabilizers.

As mentioned above, in one aspect the present invention is directed to a method for conducting an assay for platelet function activity on a whole blood sample. In one embodiment, the sample is one that has been affected by an adenosine-5-phosphate (ADP) antagonist. For example, the sample may be from a patient undergoing treatment with by an adenosine-5-phosphate (ADP) antagonist. In the present invention a combination is provided in an assay medium where the combination comprises the sample and a composition of ADP and PGE1. Usually, the final concentration of ADP is 2 to 35 µM, preferably, 15 to 20 µM and the final concentration of PGE1 is 2 to 30 nM, preferably 20 to 25 nM.

Also employed in the present methods is a reagent comprising particles coated with a compound that can result in the specific agglutination of platelets, i.e., the agglutination of platelets by the specific interaction between a receptor on the platelets and the compound on the particles. Such compounds include, by way of illustration and not limitation, antibodies to a platelet receptor and GPIIb/IIIa receptor ligands, which may be a small organic molecule, polypeptide, protein, monoclonal antibody or nucleic acid that binds, complexes or interacts with GPIIb/IIIa receptors on the platelet surface. Platelet mediated aggregation of the particles results when the GPIIb/IIIa receptors on the surface of platelets bind, complex or otherwise interact with the GPIIb/IIIa receptor ligands on the particles. Typical GPIIb/IIIa ligands include fibrinogen, monoclonal antibody 10E5 (Coller, et al., *J. Clin. Invest.* (1983) 72:325), monoclonal antibody c7E3 (The EPIC Investigators, *N. E. Journal of Med.* (1994) 330:956), von Willebrand factor, fibronectin, vitronectin and other ligands that have an arginine glycine-aspartic acid (RGD) sequence or other peptides or peptidomimetics that mimic this sequence (Cook, et al., *Drugs of the Future* (1994) 19:135). Other compounds of interest include thrombin inhibitors, low molecular weight heparin, and so forth.

The particles to which the compound is attached are at least about 0.1µ and not more than about 20µ. In one embodiment the particles are about 0.1µ to about 10µ. In another embodiment the particles are at least about 1µ and less than about 8µ. The particles can be virtually any shape, but are generally spherical with uniform diameters. The particle may have any density, but preferably of a density approximating water, generally from about 0.7 to about 1.5 g/ml. The particles may or may not have a charge on the surface, either positive or negative, preferably negative. The particles are functionalized or functionalizable so as to passively bind or attach such members at their surface, either directly or indirectly.

The particles may be solid (e.g., comprised of organic and inorganic polymers or latex), oil droplets (e.g., hydrocarbon, fluorocarbon, silicon fluid), or vesicles (e.g., synthetic such as phospholipids or natural such as cells and organelles). The solid particles are normally polymers, either addition or condensation polymers, which are readily dispersible in a liquid medium. Examples of suspendable particles are polymeric materials such as latex, lipid bilayers, oil droplets, cells and hydrogels. Other particle compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly (vinyl butyrate), polysaccharides such as dextrans and modified dextrans, etc.; either used by themselves or in conjunction with other materials. The solid particles can be comprised of polystyrene, polyacrylamide, homopolymers and copolymers of derivatives of acrylate and methacrylate, particularly esters and amides, silicones and the like.

As mentioned above, the compound is coated on the particles. Usually, the compound is passively bound to particles. Such passive binding can be accomplished by well-known techniques, commonly available in the literature. See, for example, *Immobilized Enzymes*, Ichiro Chibata, Halsted Press, New York (1978) and Cuatrecasas, *J. Biol. Chem.* (1970) 245:3059. Briefly, as mentioned above, the surface of the particle may be polyfunctional or be capable of being polyfunctionalized. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature (see above). The attachment of the side member may be directly by a bond or indirectly through the intermediacy of a linking group. The length of a linking group may vary widely, depending upon the nature of the side member and of the particle.

The ratio of molecules of compound to particle is controlled in the attachment of the molecules of compound to the particle. In one approach the number of functionalized sites on the surface of the particle may be controlled by adjusting the number of such sites introduced on the surface of the particle. Alternatively, or in conjunction with the above, the ratio of molecules of compound to particle may be controlled by adjusting the concentration of the compound in the reaction medium for the attachment. Other approaches will be suggested to one skilled in the art in view of the above teaching.

The particle reagent employed in the present invention may be treated with a sufficient amount of material to block areas of adsorption on the particles. Such materials will not affect the functioning of the particles for their intended purpose in the present invention. The blocking materials include proteins such as bovine serum albumin, bovine gamma globulin, etc., polysaccharides such as dextran, etc., and the like. In another approach, which may be utilized in conjunction with the above, particles are employed wherein the number of functionalized sites for attachment substantially reduce the adsorption area on the surface of the particles.

The particles usually comprise a label, either attached thereto or incorporated therein. The label may be any moiety that may be used for the purpose of detection. The label is often a member of a signal producing system. The label is capable of being detected directly or indirectly. The label can be isotopic or nonisotopic, usually non-isotopic, and can be a dye, fluorescent molecule, chemiluminescent molecule, a catalyst, such as an enzyme, a polynucleotide coding for a catalyst, promoter, coenzyme, enzyme substrate, radioactive group, a small organic molecule, amplifiable polynucleotide sequence, and so forth.

In one specific embodiment of the present invention, the particles contain one or more dyes that absorb in the infrared. Such dyes include bacteriochlorin, bacteriochlorophytin, meropolymethine dyes, benzoannulenes, vinylogous porphyrins, polymethine dyes, cyanines and merocyanines, and the like. Specific dyes of interest are copper (II)-tetra-tert-butyl-tetrakis(dimethylamino)-29H-31H-phthalocyanine and vanadyl-tetra-tert-butyl-tetrakis(dimethylamino)-29H-31H-phthalocyanine. The particular dye that is selected is one of convenience, availability, stability, compatibility with the particle and the like. These dyes may be incorporated directly into the particle itself, through polymerization or passive adsorption. The dyes may be loaded individually (i.e., sequentially) or in combination (i.e., simultaneously). Alternatively, the dyes may be linked to the bead in combination with the linking component, such that they do not leach from the surface. Irrespective of the loading method used, the conditions are such that the particle surface is unaffected with respect to the ability to agglutinate under appropriate conditions.

The dyes absorb light in the infrared range of about 750-900 nm, particularly in the range of about 750-850 nm. For samples with high levels of red blood cells, the light is at about 800±10 nm, which is the isosbestic point for oxyhemoglobin and reduced hemoglobin. The amount of dye employed with the particles varies with the extinction coefficient of the dye in the light range of interest, the required sensitivity of the assay, the size of the particles, the mode of binding of the dye to the particles, compatibility of the dye with the particle matrix, and the like. Usually, the amount of dye incorporated is in the range of about 1 to 20 weight percent, more usually 5 to 15 weight percent. Dyes which find a particular use in the present invention are phthalocyanines. Metal free phthalocyanines absorb at approximately 700 nm (e=162,000). The metal complexes shift the absorption to either shorter or longer wavelength, most metals shift the absorption to a much shorter wavelength, but some, such as lead absorb at much longer wavelength than the metal free phthalocyanines.

The complexes formed between transition metals and phthalocyanines (metollophthalocyanines and metallonaphthalocyanines) are chemically very stable to light and heat. They are formed by condensation of opthalodinitriles in the presence of an appropriate metal. Some of the metals used in the formation of the metollophthalocyanines besides copper (Cu) and vanadium (V) are magnesium (Mg), zinc (Zn), and cobalt (Co).

In one specific embodiment of the invention carboxylated microparticles with a flat absorption maximum are employed. These microparticles are prepared by incorporating multiple dyes that have distinct absorption maximum close to 805 nm. This results in a flat maximum absorption spectrum across a broad range wavelength from 780-820 nm.

The sample may be any solution, synthetic or natural, to be analyzed where the sample has been subject to an effect from a P2Y12 antagonist, particularly, a thienopyridine, potentially in combination with aspirin. The term sample includes biological tissue, including body fluids, from a host, and so forth. The sample can be examined directly or may be pretreated, usually. The present invention has particular application to samples that comprise platelets, including body fluids such as, for example, whole blood, platelet-containing blood fractions such as plasma, and the like. In one embodiment the invention has particular application to whole blood samples. The amount of the sample depends on the nature of the sample. For fluid samples such as whole anticoagulated blood, the amount of the sample is usually about 30 µl to 5 ml, preferably, about 100 to 300 µl. The term "sample" includes unprocessed samples directly from a patient or samples that have been pretreated and prepared in any convenient liquid medium, usually an aqueous medium (e.g., sodium citrate).

Preferably, the medium for conducting the assays in accordance with the present invention is an aqueous medium. Other polar cosolvents may also be employed in the medium, usually oxygenated organic solvents of from 1-6, more usually from 1-4 carbon atoms, including alcohols, ethers and the like. Usually, such cosolvents are present in less than about 70% by weight, more usually, in less than about 30% by weight. Additionally, various ancillary materials are frequently employed in the method in accordance with the present invention. For example, buffers are normally present in the assay medium, as well as stabilizers for the assay medium and the assay components; surfactants, particularly non-ionic surfactants; binding enhancers, e.g., polyalkylene glycols; or the like.

The pH for the medium is usually in the range of about 2 to about 11, preferably, about 4 to about 9. Various buffers may be used to achieve the desired pH and maintain the pH during the method. Illustrative buffers include HEPES, borate, phosphate, carbonate, Tris, barbital, and the like. The particular buffer employed is not critical to the method but one buffer may be preferred over others in certain circumstances. In some circumstances HEPES is preferred and is present at a concentration of about 0.05 M to about 1 mM but generally at a concentration of about 0.01 M.

The volume of assay medium is about 25 µl to about 500 µl usually about 75 µl to about 25 µl. The assays may be carried out in any suitable container. Conveniently, the container is a cuvette or cartridge that is used with the instrument for carrying out the assay and measuring the assay results. The reaction container usually contains the activation initiator in accordance with the present invention in dry lyophilized form together with other reagents such as the particle reagent and the like, stabilizers and so forth.

The combination of sample and particle reagent is incubated under conditions for agglutinating the particles. Moderate temperatures are normally employed for carrying out the method. The temperature may be constant or may vary. Usually, a constant temperature is employed during the reaction step. The temperature employed is usually about 10 to about 80° C., more usually, about 15 to about 45° C., preferably, the temperature should be at least 25° C., more preferably in the range of about 30 to about 40° C., usually about 37° C.

The extent of agglutination of the particles is determined and is related to the presence and/or amount of the P2Y12 antagonist in the sample. The presence of agglutination may be determined visually by observing clumping of the particles, which would indicate agglutination. Preferably, as mentioned above, the particles may be colored to aid in visualizing agglutination or clumping of the matrix. The extent of agglutination may be measured spectrophotometrically, turbidimetrically, nephelometrically, etc., by observing the rate of change of optical density of the medium, and so forth.

In a specific embodiment of the present invention an assay for platelet function activity is conducted on a whole blood sample from a patient undergoing treatment with a thienopyridine. The sample is combined in a suitable container, e.g., reaction cuvette, with fibrinogen coated particles, and the composition of ADP and PGE1 to form an assay medium. The particles of the particle reagent have one or more infrared dyes incorporated therein. The combination is subjected to conditions conducive to agglutination, and the medium is irradiated with infrared light. The transmission of infrared light from the assay mixture is determined where the level of transmission is related to platelet reactivity.

The agglutination medium is selected to have high absorption at about 800 nm. The ratio between the agglutination medium absorption coefficient and whole blood absorption coefficient should preferably be greater than about 4:1 at 800 nm. The absorption ratio for a particular assay is a function of both the absorption coefficient of the agglutination medium and the concentration of the agglutination medium in the assay sample.

After the sample has been combined with the reagents, desirably it will be heated to a temperature above room temperature, but below that which would interfere with the assay, so as to insure that the temperature can be controlled without adversely affecting the assay result. Desirably, the temperature should be at least 250, preferably in the range of 30-40° C., more preferably about 37° C. The reaction medium is usually gently agitated upon combining of the reagents with the sample and during the period of the reaction. Agitation is sufficient to achieve and maintain homogeneity in the assay samples. The total time of the readings from the zero time (time of mixing), may range from about 10 sec. to 10 min., more usually about 30 sec. to 8 min., and preferably about 30 sec. to 3 min. The data may be analyzed by any convenient means, particularly using an algorithm that can manipulate the data in relation to calibrators and/or controls.

The level of agglutination is an indication of the platelet reactivity of the sample tested. The level of agglutination may be compared against a standard of known platelet reactivity. Usually, the result will be compared to a calibrator, which may be performed concomitantly or have been performed previously or may be provided as a standard curve. In individuals treated with a drug-eluting stent (DES), platelet reactivity may be used to assess the likelihood of adverse post-discharge outcomes, including stent thrombosis.

The method of the present invention may be employed in conjunction with an assay for platelet count such as that described in U.S. patent application Ser. No. 09/177,884 filed Oct. 23, 1998 and International Application No. PCT/US1999/24670 filed Oct. 20, 1999 (Pub. No. WO/2000/025140), the relevant disclosures of which are incorporated herein by reference.

The above assays preferably may be conducted in a device, which allows the reactions in accordance with the present invention to occur and which measures the results thereof. The instrument should assess platelet function based upon the ability of activated platelets to bind fibrinogen. As activated platelets bind and agglutinate fibrinogen-coated particles, there is an increase in light transmittance. In general, an instrument to measure the result of the assay is one that can measure agglutination. Preferably, the instrument measures a change in optical signal due to agglutination. Suitable instruments include, by way of illustration and not limitation a kinetic spectrophotometer, VERIFYNOW™ System instrument (commercially available from Accumetrics, Inc., San Diego, Calif. and employed for rapid platelet function activity measurements on normal samples), or the like.

The VerifyNow™ System instrument is a turbidimetric-based optical detection system that measures platelet induced aggregation as an increase in light transmittance. The system includes an analyzer, disposable cartridge and controls. The cartridge contains reagents based on microparticle agglutination technology. The quality control system includes an electronic control, two levels of assayed "wet" controls (WQC), an in-cartridge humidity sensor, an in-packaging temperature indicator, and a test for concurrence of two assay channels. The analyzer controls assay sequencing, establishes the assay temperature, controls the reagent-sample mixing for the required duration, determines the degree of platelet function, displays the result and performs self-diagnostics. For use in the present methods the test cartridge of the system contains a lyophilized preparation comprising particles with passively bound GPIIb/IIIa receptor ligand, a composition of ADP and PGE1, and buffer. The patient sample is usually citrated whole blood, which is automatically dispensed from the blood collection tube into the cartridge by the analyzer, with no blood handling required by the user. The interaction is monitored by the infrared absorbency characteristics of the particles. As the particles interact with the platelets, the agglutination of the particles is measured through the optical system of the VerifyNow™ analyzer. The agglutination is detected as an increase in the transmission of infrared light through the sample. The reaction kinetics are analyzed and translated into "P2Y12 Response Units", PRU.

In another embodiment of the present invention is a kit that includes in packaged combination a lyophilized preparation comprising particles with passively bound fibrinogen, composition of ADP and PGE1, and buffer. The lyophilized preparation may be present in a reaction container such as a cartridge used in the instrument of analysis. For the aforementioned VerifyNow™ System, the lyophilized preparation may be placed in the outer wells of the four-well cartridge used in the analyzer. The kit may also include a sample collection container and/or a device for carrying out the present method. The relative amounts of reagents may be varied widely to provide for concentrations in solution of the reagents that substantially optimize the sensitivity of a determination.

Where appropriate, the reagents can be placed in an air-tight package in order to maintain the activity of any reagents. The package may be, for example, a bag, pouch, or the like fabricated from a material that is substantially non-permeable to moisture. Such materials include, by way of example and not limitation, plastic, aluminum foil, and the like. For blood samples the kit may also include an article for piercing a person's skin, disinfectant or sterilizing pads and so forth. The kit may also include calibrators and standards. Furthermore, the kit may also include one or more reagents for conducting an assay for platelet count.

The kit can include the reagents necessary for carrying out the assay of the present invention. In one embodiment, the kit includes a blood vial, a buffer that maintains the pH and salt concentration of the blood sample assessed within ranges suitable for platelet mediated agglutination of the solid surface and small polymeric beads coated with platelet GPIIb/IIIa receptor ligand. The buffer can be in solution, or can consist solely of the buffering composition and salts to which a known amount of water is added to give the desired buffer solution. Optionally, the kit can also comprise an anticoagulant. In one embodiment, the buffer is HEPES; the anticoagulant is citrate; a GPIIb/IIIa receptor ligand is fibrinogen; small polymeric beads are polyacrylonitrile or carboxylated polystyrene in which a peptide GPIIb/IIIa receptor ligand, such as fibrinogen, is passively bound to the bead surface by means of a hydrophobic and/or hydrogen bond interaction between the peptide and a functional group on the bead surface. In a further embodiment, the kit additionally comprises a platelet activator, such as a composition of ADP and PGE1.

In one embodiment of the present invention, a determination is made for the relationship between the response to clopidogrel, post-treatment reactivity (as defined by either percent inhibition of platelet function relative to baseline or absolute reactivity as measured by PRU) and adverse events using point-of-care testing for patients undergoing PCI receiving a DES, with a blood sample taken prior to discharge.

In another embodiment, increased dosing of clopidogrel may be considered in PCI patients with DES who weigh more than about 100 kg. Point-of-care testing of platelet function at the time of PCI may identify patients at high-risk for stent thrombosis over 30-day follow-up. At-risk patients can benefit from increased clopidogrel dosing regimens or alternative anti-platelet strategies (e.g., prasugrel).

EXAMPLES

The following examples are intended to illustrate the invention but are not intended to limit its scope. Parts and percentages are by weight unless otherwise indicated.

Example 1

Dose response testing was performed with ADP (Chronolog Corp., Havertown, Pa.) and PGE1 (SIGMA) at 20 µM and 22 nM final concentrations respectively. ADP was diluted in Hepes/Saline, pH 7.4 buffer to a final concentration of 200 µM prior to use on the aggregometer. PGE1 was diluted in Hepes/Saline, pH 7.4 buffer to a final concentration of 220 nM prior to use on the aggregometer. A P2Y12 receptor antagonist was diluted in DMF to final concentrations of 1 mM, 2 mM and 5 mM.

Five microliters of the diluted P2Y12 antagonist were spiked into 5 mL whole blood. Samples were inverted and incubated for one hour at room temperature. The whole blood baseline sample did not receive any additive. Once incubation was complete, whole blood samples were spun at 1500 rpm for 15 minutes for platelet rich plasma (PRP) and 3500 rpm for 15 minutes for platelet poor plasma (PPP). Platelet count was adjusted to approximately 250,000/µL for each sample using PPP.

For aggregometry, 450 µL of adjusted PRP was added to the glass cuvette. The blank sample contained 450 µL PPP and 50 µL Hepes/Saline buffer. Fifty microliters of a composition of 200 µM ADP and 220 nM PGE1 was added to each PRP sample and tested for ten minutes on the aggregometer.

Figure 2:
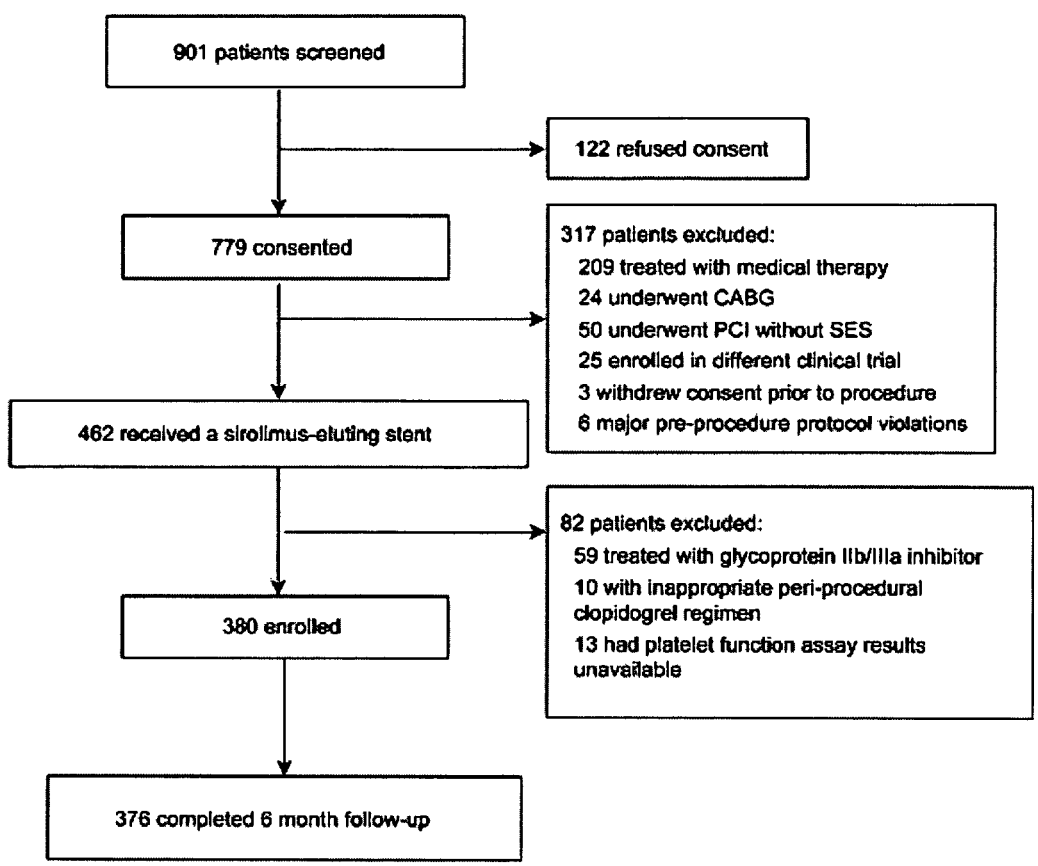
FIG. 2 shows the flow diagram of the clinical study described in Example 3 (CABG, coronary artery bypass grafting; PCI, percutaneous coronary intervention; SES, sirolimus-eluting stent).

As illustrated in FIG. 1, the above reagents and system successfully detects the extent of platelet aggregation from a blood sample treated with a P2Y12 antagonist. FIGS. 1 and 2 illustrate the mean response of one individual and five individuals, respectively.

It is evident from the above results illustrated in FIG. 1 that a simple, rapid method is provided by the present invention for conducting an assay for platelet activity on samples that have been affected by exposure to a P2Y12 antagonist.

Example 2

A study of PCI patients was conducted. The patients selected had at least one of the following, at least one lesion ≥50% diameter stenosis requiring PCI, a reference vessel diameter between 2.25 and 4.0 mm, target lesion located within a native coronary artery or bypass graft that was either de novo or restenotic and no known allergy to aspirin, clopidogrel, or any component of an DES.

Whole blood was obtained from the side port of the arterial sheath prior to anticoagulant or anti-thrombin therapy and by phlebotomy 12 hours post-PCI. The inhibitory effect of clopidogrel was measured using the VerifyNow™ P2Y12 assay (Accumetrics, Inc., San Diego, Calif.). The percentage inhibition induced by clopidogrel in patients with a baseline sample prior to clopidogrel exposure was calculated using the formula: 1−(PRU post-clopidogrel/PRU baseline)×100.

If the post-treatment ADP-induced aggregation was greater after clopidogrel than at baseline, the percentage inhibition was considered to be zero. In patients without a baseline sample prior to clopidogrel exposure (i.e., patients on chronic clopidogrel therapy prior to PCI), the percentage inhibition reported by the device using the internal reference channel was used.

All patients received 325 mg uncoated aspirin the day of the procedure regardless of previous aspirin use. Patients not previously taking clopidogrel were treated with a 600 mg loading dose at the conclusion of the procedure before leaving the catheterization laboratory. Either intra-procedural heparin (with a goal activated clotting time of >250 sec) or bivalirudin were administered during the procedure at operator discretion. Patients were instructed to take aspirin 325 mg/day indefinitely, and clopidogrel 75-mg/day for a minimum of 3 months. Patients receiving glycoprotein IIb/IIIa inhibitors or who had received a loading dose of clopidogrel within 24 hours prior to the procedure were excluded from analysis.

"High post-treatment reactivity" was defined as the highest quartile of absolute PRU while on clopidogrel (on chronic therapy or 12 hours after loading dose), whereas "clopidogrel non-responsiveness" was defined as the lowest quartile of percent inhibition of platelet function (relative change in platelet reactivity after clopidogrel compared to the patient's baseline or the reference channel). Patients were judged to be insulin resistant if their Homeostasis Model Assessment index, calculated as: [fasting insulin ($\mu$U/mL)]*[fasting glucose (mg/dl)]/405, was >3.0 or if they had diabetes requiring medication.

The clinical endpoints measured were death, MI (non-Q-wave and Qwave) and stent thrombosis. Peri-procedural non-Q wave myocardial infarction (MI) was defined as CK-MB>3 times the upper limit of normal in the absence of pathological Q waves. MI during the 30-day follow-up period was defined as any elevation in cardiac enzymes considered due to ischemia by the clinical events committee. "Stent thrombosis" was defined as any of the following: angiographic demonstration of stent closure or thrombus, unexplained sudden death, MI without concomitant documentation of a patient stent. "Acute thrombosis" was defined as thrombosis occurring within 24 hours of the PCI, and "subacute thrombosis" as occurring between 24 hours and the 30-day follow-up.

The computer-based analysis program SPSS (Statistical Package for the Social Sciences, 12.0 for PC, SPSS Inc., Chicago, Ill.) was used for statistical calculations. The chi-square test, or Fisher exact test when any expected cell count was <5 for a 2 by 2 table, were used to detect differences in categorical variables; p<0.05 was considered significant. Comparison of continuous variables was performed using Student t-test. Univariate and forward conditional (entry criteria of 0.05 and exit criteria of 0.10) multivariate logistic regression analyses were performed to identify characteristics or variables independently associated with clopidogrel non-responsiveness.

The following variables were tested and entered into the multivariate analysis if the p value was >0.10 on univariate analysis, age, gender, weight, body mass index (BMI)≥30 kg/m$^2$, history of diabetes, insulin resistance, history of CHF, history of MI, history of HTN, current smoking, renal insufficiency (creatinine≥1.5), EF<40%, presentation with MI, presentation with angina, bivalirudin use, and prior use of aspirin, beta-blockers or atorvastatin.

Baseline clinical baseline clinical characteristics are in Table 1 below.

TABLE 1

|  | N = 280 |
| --- | --- |
| Mean age (yrs) | 68 ± 11 |
| Male gender | 213 (76%) |
| Diabetes mellitus | 75 (27%) |
| History of CHF | 28 (10%) |
| Previous MI | 82 (29%) |
| Current smoker | 28 (10%) |
| Weight (kg) | 89.5 ± 24.9 |
| Body Mass Index (kg/m$^2$) | 29.8 ± 7.8 |
| Medical therapy | |
| Chronic aspirin | 242 (86%) |
| Chronic clopidogrel | 101 (36%) |
| Beta-blocker | 171 (61%) |

The indications for a procedure were determined by one of the following, stable angina or ischemia in 261 patients (93%), unstable angina in 13 patients (4.8%), acute MI in 6 patients (2.2%).

The lesion characteristics are listed in Table 2.

TABLE 2

|  | N = 454 |
| --- | --- |
| Lesion length | 19.9 mm |
| Pre-TIMI grade 0-2 flow | 8.6% |
| Lesion score B2/C | 66% |
| Chronic total occlusion | 4.8% |
| Bifurcation lesion | 16% |
| Saphenous vein graft | 6.6% |
| Unprotected LMCA | 1.1% |

The procedural characteristics are in Table 3.

TABLE 3

|  | N = 454 |
| --- | --- |
| No. of lesions treated | 1.7 ± 0.8 |
| No. of vessels treated | 1.4 ± 0.6 |
| Stented length (mm) | 30.1 ± 20.2 |
| No. of stents per lesion | 1.5 ± 0.8 |
| Mean stent diameter (mm) | 2.9 ± 0.3 |
| Post-TIMI grade 0-2 flow | 0.6% |
| IVUS guidance post-stent | 13% |
| Rotablator performed | 1.5% |
| Bivalirudin used | 41% |

Clopidogrel non-responsiveness was defined by a percent inhibition <10%. Univariate predictors of clopidogrel non-responsiveness were presentation with MI (p=0.03), history of diabetes mellitus (p=0.03), body weight in the highest quartile (>100 kg, p=0.03) and beta-blocker use (p=0.001).

The multivariate predictors for clopidogrel non-responsiveness are in Table 4.

TABLE 4

| Variable | Odds Ratio (Conf. Interval) | p Value |
| --- | --- | --- |
| Presentation with MI: | 6.8 [95% 1.1 to 41.5] | 0.038 |
| Heavy weight* | 2.0 [95% 1.1 to 3.8] | 0.033 |
| Beta Blocker Use | 2.5 [95% 1.3 to 4.9] | 0.006 |

*Heaviest quartile of weight, >100 kg.

Stent thrombosis at 30 day follow-up is reported in Table 5.

TABLE 5

|  | N = 280 |
| --- | --- |
| Clop NR: | p = 0.046 |
| High post-Rx reactivity: | p = 0.06 |
| Clop NR + high post-Rx reactivity: | p = 0.02 |

Stent thrombosis was found in a number of patients. All patients were taking dual antiplatelet therapy at the time of the thrombosis. Patient No. 1 had acute thrombosis 80 minutes after PCI, and was on clopidogrel at the time of the procedure. The percentage of inhibition for patient No. 1 was 0%. Patient No. 2 had sub-acute thrombosis 6 days following PCI and was on clopidogrel at the time of procedure. The percentage of inhibition for patient No. 2 was 0%. Patient No. 3 had sub-acute thrombosis 34 days following- PCI, was clopidogrel naïve and loaded with 600 mg at the time of the procedure. The percentage inhibition for Patient No. 3 was 0%. Patient No. 4 had sub-acute thrombosis 8 days following PCI, was clopidogrel naïve and loaded with 600 mg at the time of the procedure. The percentage inhibition for patient No. 4 was 44%. All four patients with thrombosis and non-response were in the highest quartile of absolute post-clopidogrel reactivity.

In this example, one quarter of patients undergoing PCI had clopidogrel-induced platelet inhibition, defined as <10% as measured by a point-of-care assay. Patients presented with MI had heavier weight, and beta-blocker use was independently associated with clopidogrel non-responsiveness. Clopidogrel non-response was significantly associated with stent thrombosis over a 30 day follow-up, particularly in the setting of high absolute post-treatment reactivity.

From this example, it is noted that dosing of clopidogrel should be increased for patients greater than 100 kg. Additionally, point-of-care testing of platelet function, at the time of PCI, can be used to identify patients at high-risk for stent thrombosis over a thirty day follow-up. At-risk patients can benefit from increased clopidogrel dosing regimens or alternative anti-platelet strategies, including but not limited to prasugrel and the like.

Example 3

Another study was conducted to determine whether platelet reactivity in patients on clopidogrel therapy as assessed by the VerifyNow™ P2Y12 assay (Accumetrics, Inc., San Diego, Calif.) is associated with post discharge outcomes, including stent thrombosis, after drug-eluting stent (DES) implantation. This study was published in Price, et al., *Eur. Heart J.* (2008) 29(8):992-1000, which is fully incorporated herein.

Patients were eligible for enrolment if they had at least one lesion ≥50% diameter stenosis requiring PCI and had no known allergy to aspirin, clopidogrel, or a sirolimus-eluting stent (SES). Patients on clopidogrel therapy or who were clopidogrel naïve were eligible for inclusion. However, to ensure that those patients on clopidogrel therapy prior to the procedure were optimally and consistently treated at the time of platelet function assessment, only those patients who had received a loading dose of 600 mg at least 12 h prior to the procedure or were on a maintenance dose of clopidogrel 75 mg/day for more than 5 days were included. Patients receiving peri-procedural glycoprotein inhibitors were not enrolled due to interference with the P2Y12 assay.

Whole blood was obtained at the time of catheterization from the side-port of the arterial sheath prior to anticoagulant therapy in patients on previous clopidogrel therapy and by phlebotomy 12 h after PCI and a 600 mg clopidogrel loading dose in patients who were clopidogrel naïve. Blood was placed into 1.8 mL-draw plastic Vacuette® tubes (Greiner, Monroe, N.C.) containing 3.2% sodium citrate.

The inhibitory effect of clopidogrel was measured using the VERIFYNOW™ P2Y12 assay (Accumetrics, Inc.). VerifyNow™ P2Y12 is a rapid platelet function cartridge-based assay designed to measure directly the effects of drugs on the P2Y12 receptor. The assay contains 20 mM ADP and 22 nM prostaglandin E1 to reduce the activation contribution from ADP binding to P2Y1 receptors. Fibrinogen-coated microparticles are used in the VerifyNow™ P2Y12 cartridge to bind to available platelet receptors. The VerifyNow™ instrument measures platelet-induced aggregation as an increase in light transmittance and utilizes a proprietary algorithm to report values in P2Y12 reaction units (PRU). With this assay, a higher PRU reflects greater ADP-mediated platelet reactivity. The mean coefficient of variation of test precision has been reported to be 3.2% in patients with coronary artery disease.

Interventional strategy was at the discretion of the operator. Either intra-procedural unfractionated heparin (with a goal-activated clotting time>250 s) or bivalirudin was used during the procedure. All patients received SES, and they received aspirin 325 mg on the day of the procedure regardless of previous aspirin use. Patients not previously on clopidogrel received a 600 mg loading dose at the conclusion of the procedure before leaving the catheterization laboratory. Patients already receiving clopidogrel therapy (as noted in the inclusion/exclusion criteria earlier) did not receive an additional loading dose. Patients were instructed to take aspirin 325 mg indefinitely and clopidogrel 75 mg daily for a minimum of 3 months post-procedure.

"Post-treatment platelet reactivity" was defined as the PRU on clopidogrel (12 h after PCI and a 600 mg loading dose in patients not previously on clopidogrel, or at the time of catheterization prior to PCI in patients already on clopidogrel). "Technical success" was defined as a final diameter stenosis ≤30% and thrombolysis in myocardial infarction (TIMI) flow grade 3. Clinical endpoints measured were cardiovascular (CV) death, non-fatal myocardial infarction (MI), and stent thrombosis. "MI over follow-up" was defined as any typical rise and fall of cardiac biomarkers in the setting of clinical signs or symptoms consistent with cardiac ischaemia, following the American College of Cardiology definition (Cannon, et al., *J. Am. Coll. Cardiol.* (2001) 38:2114-2130). The Academic Research Consortium definitions were used for "stent thrombosis" (definite, probable, and possible) (Mauri, et al., *N. Engl. J. Med.* (2007) 356:1020-1029). "Subacute stent thrombosis" was defined as stent thrombosis occurring after discharge to 30 day follow-up, and late-stent thrombosis was defined as stent thrombosis occurring between 30 day and 6 month follow-ups.

The computer-based analysis program SPSS (Statistical Package for the Social Sciences, 12.0 for PC, SPSS Inc., Chicago, Ill., USA) was used for statistical calculations. Randomized studies of stent implantation with and without thienopyridine therapy have demonstrated a 75-85% relative reduction in cardiac events in patients treated with dual antiplatelet therapy compared with aspirin alone. We estimated a sample size of 380 patients would provide 70% power to detect an 80% relative difference in the rate of events using a one-sided Fisher's exact test, assuming an event rate of 1.0% in responders and a clopidogrel non-responsiveness rate of one-third. Comparison of continuous variables was performed using Student's t-test. The $\chi^2$ test was used to detect differences in categorical variables, and a Fisher's exact test was used when any expected cell count was <5 for a 2 by 2 table. The Kolmogorov-Smirnov test was used to test for normality. A receiver-operating characteristic (ROC) curve analysis was used to determine the ability of the VERIFYNOW™ P2Y12 assay to distinguish between patients with and without post-discharge events after PCI. The optimal cut-off point was calculated by determining the post-treatment PRU that provided the greatest sum of sensitivity and specificity. Bootstrap validation was performed using R software. Survival curves were generated using the Kaplan-Meier method, and the difference between curves was assessed by log-rank test. A P-value<0.05 was considered significant.

A total of 380 patients were enrolled in this study (see FIG. 2). Baseline clinical, lesion, and procedural characteristics are shown in Tables 6 and 7. Overall, the average age was 68±11 years, 76.8% were male, 14.2% had renal insufficiency, 28.9% were diabetic, and 44.5% were on clopidogrel therapy at the time of PCI. The procedural indication was stable angina or ischaemia in most patients (93.9%). An average of 1.7±0.8 lesions per patient were treated. The mean lesion length was 20.0±13.1 mm, and a mean of 1.4±0.7 SESs were implanted per lesion. Technical success was achieved in all patients.

Clinical follow-up at 6 months was complete in 98.9% of patients. After discharge, there were three CV deaths (0.8%), two of which were sudden (84 and 186 days post-procedure). There was one non-CV death (due to sepsis) 32 days post-procedure. Non-fatal MI occurred in five patients (1.3%). There were six episodes of stent thrombosis (1.6%): three were definite subacute, one was definite late, and two were possible late-stent thromboses. The combined endpoint of CV death, non-fatal MI, or stent thrombosis occurred in

TABLE 6

Baseline clinical characteristics of the study population.

| Characteristic | Overall group (n = 380) | Lower reactivity* (n = 258) | High reactivity* (n = 122) | P-value |
|---|---|---|---|---|
| Age, years | 68 ± 11 | 67 ± 11 | 70 ± 10 | 0.01 |
| Male gender, n (%) | 292 (76.8) | 201 (77.9) | 91 (74.6) | 0.5 |
| Diabetes mellitus, n (%) | 110 (28.9) | 59 (22.9) | 51 (41.8) | 0.001 |
| Previous MI, n (%) | 120 (31.6) | 77 (29.8) | 43 (35.2) | 0.3 |
| History of hypertension, n (%) | 335 (88.2) | 225 (87.2) | 110 (90.2) | 0.4 |
| History of congestive heart failure, n (%) | 36 (9.5) | 21 (8.3) | 15 (12.0) | 0.2 |
| LVEF <40%, n (%) | 34 (9.5) | 22 (9.2) | 14 (10.3) | 0.7 |
| Renal insufficiency (creatinine >1.5), n (%) | 54 (14.2) | 31 (12.0) | 23 (18.9) | 0.08 |
| Current smoker, n (%) | 34 (8.9) | 25 (9.7) | 9 (7.4) | 0.5 |
| Body mass index, kg/m$^2$ | 29.6 ± 6.9 | 29.3 ± 6.6 | 30.2 ± 7.6 | 0.2 |
| Concomitant medications, n (%) | | | | |
| ACE-inhibitor | 140 (36.8) | 91 (35.3) | 49 (40.2) | 0.4 |
| Beta-blocker | 241 (63.4) | 151 (58.5) | 90 (73.8) | 0.004 |
| Atorvastatin | 135 (35.5) | 95 (36.8) | 40 (32.8) | 0.4 |
| Aspirin | 328 (86.3) | 223 (86.4) | 105 (86.1) | 1.0 |
| Stable angina/ischaemia | 356 (93.7) | 242 (93.8) | 114 (93.4) | 1.0 |

*High reactivity defined as post-treatment reactivity above the optimal cut-off point by ROC curve analysis (PRU ≥ 235) and lower reactivity below this threshold.

TABLE 7

Lesion and procedural characteristics.

| Characteristic | Overall group (n = 380) | Lower reactivity* (n = 258) | High reactivity* (n = 122) | P-value |
|---|---|---|---|---|
| Number of lesions per patient | 1.7 ± 0.8 | 1.7 ± 0.8 | 1.5 ± 0.7 | 0.01 |
| Number of vessels per patient | 1.4 ± 0.5 | 1.4 ± 0.6 | 1.3 ± 0.5 | 0.1 |
| Lesion type, n (%) | | | | |
| AHA/ACC type B2/C | 299 (78.7) | 205 (79.2) | 94 (77.7) | 0.7 |
| Bifurcation | 92 (24.2) | 62 (24.0) | 30 (24.8) | 0.9 |
| Saphenous vein graft | 31 (8.2) | 18 (7.0) | 13 (10.7) | 0.2 |
| Chronic total occlusion | 26 (6.8) | 16 (6.2) | 10 (8.2) | 0.5 |
| Thrombus-containing lesion | 4 (1.1) | 3 (1.2) | 1 (0.8) | 1.0 |
| Number of stents per lesion | 1.4 ± 0.7 | 1.4 ± 0.8 | 1.4 ± 0.7 | 0.3 |
| Stent diameter, mm | 2.86 ± 0.36 | 2.84 ± 0.35 | 2.91 ± 0.38 | 0.004 |
| Stent length per lesion, mm | 30.3 ± 20.2 | 30.6 ± 20.9 | 29.6 ± 18.5 | 0.5 |
| Maximum balloon inflation, atm | 16.6 ± 2.2 | 16.5 ± 2.3 | 16.7 ± 2.0 | 0.3 |
| IVUS performed, n (%) | 150 (39.5) | 105 (40.5) | 45 (37.2) | 0.5 |
| Bivalirudin used, n (%) | 152 (40.0) | 108 (41.9) | 44 (36.1) | 0.3 |

Post-treatment PRU was normally distributed (one sample Kolmogorov-Smirnov test, P=0.2). The mean post-treatment reactivity was 184±85 PRU. There was no difference in posttreatment reactivity between patients on previous clopidogrel therapy and clopidogrel-naïve patients receiving a loading dose (186±73 vs. 183±94 PRU, P=0.7), nor was there a difference in reactivity between patients receiving intra-procedural heparin or bivalirudin (184±86 vs. 184±84 PRU, P=1.0).

10 patients (2.6%). None of these patients had suboptimal angiographic results or angiographic evidence of residual dissection during the index procedure. One patient who suffered a subacute stent thrombosis 8 days post-PCI did not take clopidogrel after discharge (i.e., no clopidogrel beyond 24 h following the procedure). All other events occurred while patients were taking dual-antiplatelet therapy. The post-treatment reactivity of the patients who had stent thrombosis while taking antiplatelet therapy were 283, 292, 236, 244, and 271 PRU. A total of 373 patients (98.2%) were on maintenance clopidogrel therapy at 3 months post procedure, and 317 patients (83.4%) were on maintenance therapy at 6 months follow-up. Table 8 demonstrates the event rates in patients who were receiving clopidogrel therapy through 6 month follow-up, and Table 9 demonstrates the 6 month event rates in patients completing a minimum 3 month course of clopidogrel therapy. Patients with adverse events had significantly higher platelet reactivity than those who did not (242 vs. 186 PRU, one-tailed t-test P=0.03).

TABLE 8

Six month out-of-hospital outcomes in patients on clopidogrel therapy through 6 month follow-up.

|  | Overall group (n = 317) | Lower reactivity (n = 258) | High reactivity (n = 108) | P-value* |
|---|---|---|---|---|
| CV death, n (%) | 3 (0.9) | 0 | 3 (2.8) | 0.04 |
| Non-fatal MI, n (%) | 4 (1.3) | 2 (1.0) | 2 (1.9) | 0.6 |
| Stent thrombosis, n (%) | 5 (1.6) | 0 | 5 (4.6) | 0.004 |
| CV death, non-fatal MI, stent thrombosis, n (%) | 9 (2.8) | 2 (1.0) | 7 (6.5) | 0.008 |

*Comparison between groups with high and lower reactivity (Table 6).

TABLE 9

Six month out-of-hospital outcomes in patients on clopidogrel therapy for a minimum of 3 months post-procedure.

|  | Overall group (n = 373) | Lower reactivity (n = 252) | High reactivity (n = 121) | P-value* |
|---|---|---|---|---|
| CV death, n (%) | 3 (0.8) | 0 | 3 (2.5) | 0.03 |
| Non-fatal MI, n (%) | 4 (1.1) | 2 (0.8) | 2 (1.7) | 0.6 |
| Stent thrombosis, n (%) | 5 (1.3) | 0 | 5 (4.1) | 0.003 |
| CV death, non-fatal MI, stent thrombosis, n (%) | 9 (2.4) | 2 (0.8) | 7 (5.8) | 0.006 |

*Comparison between groups with high and lower reactivity (Table 6).

Figure 3:
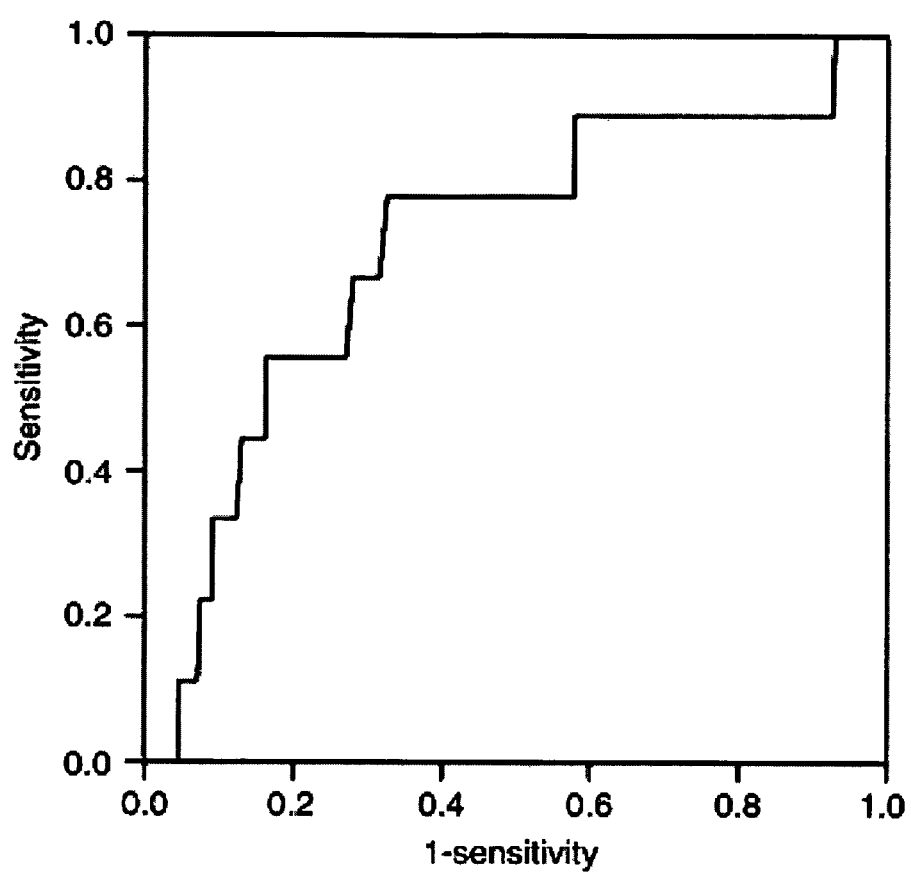
FIG. 3 illustrates the receiver-operating characteristic (ROC) curve for the VERIFYNOW™ P2Y12 assay. An area under the curve of 0.711 was observed (P=0.03).

An ROC curve analysis of post-treatment platelet reactivity in the patients who maintained clopidogrel therapy through 6 month follow-up demonstrated that post-treatment PRU was able to distinguish between patients with and without subsequent events [area under the curve 0.711 [95% confidence interval 0.529-0.893), P=0.03] (FIG. 3). A PRU≥235 was identified as the optimal cut-off value to predict post-discharge 6 month outcomes, providing a sensitivity of 78% (95% CI 46-94), specificity of 68% (95% CI 67-69), and a negative predictive value of 99% (95% CI 98-100). By bootstrap analysis using 10 000 replicates, the bounds for the 95% confidence interval of the optimal cut-off was 174-291 PRU. The optimal cut-off was 235 PRU (95% CI by bootstrapping 174-291 PRU) in the cohort of patients who completed at least 3 months of clopidogrel [area under the curve 0.720 (95% confidence interval 0.540-0.900), P=0.02; sensitivity 78% (95% CI 46-94), specificity 70% (95% CI 69-70)]. This cut-off was similar to the boundary of the upper tertile of post-treatment reactivity (>231 PRU). Patients with post-treatment reactivity above the optimal cut-off value were considered to have 'high' post-treatment reactivity. Patients with high post-treatment reactivity were significantly older, more likely to be diabetic, tended to have renal insufficiency, and were more likely to be taking a beta-blocker than patients with lower post-treatment reactivity (Table 6). Patients with high post-treatment reactivity also had fewer lesions per patient and had on average a larger diameter stent implanted (Table 7).

Figure 4:
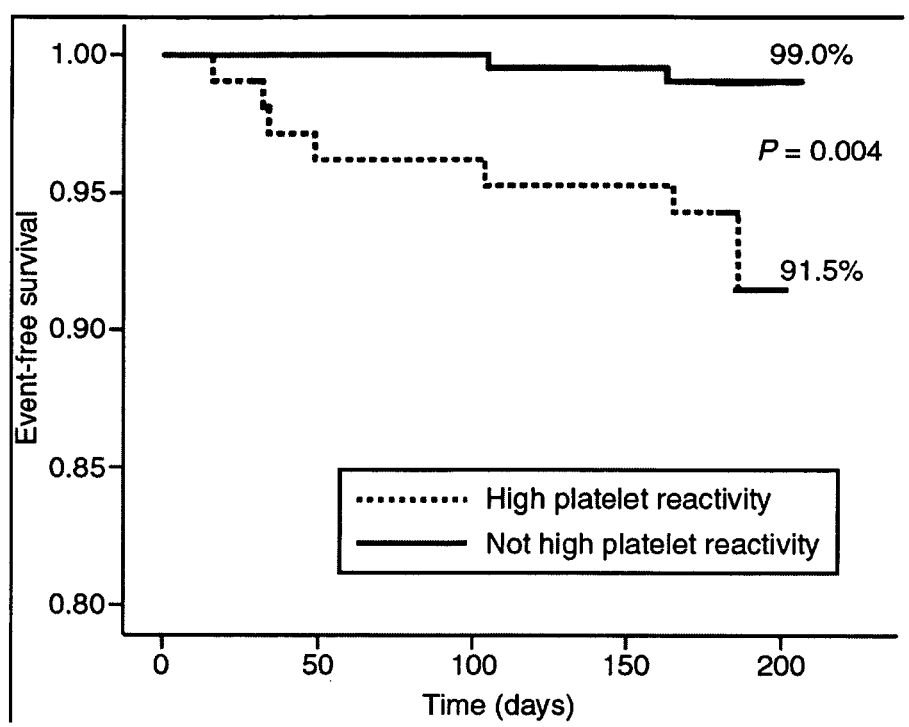
FIG. 4 illustrates survival free of out-of-hospital cardiovascular death, non-fatal myocardial infarction, and stent thrombosis in patients with and without high post-treatment reactivity.

Patients with high post-treatment reactivity had significantly greater rates of CV mortality (2.8 vs. 0%, P=0.04), any stent thrombosis (4.6 vs. 0%, P=0.004), definite or probable stent thrombosis (2.8 vs. 0%, P=0.04), and the combined endpoint of CV death, non-fatal MI, or stent thrombosis (6.5 vs. 1.0%, P=0.008) (Tables 8 and 9). The difference in outcomes was still significant when considering all-cause death, non-fatal MI, or stent thrombosis (6.5 vs. 1.4%, P=0.035). The event-free survival curves are shown in FIG. 4. The survival rate free from the combined endpoint of CV death, non-fatal MI, or stent thrombosis was 91.4% in patients with high post-treatment reactivity and 99.0% in patients without high post-treatment reactivity (P=0.004).

In this example, an ROC analysis was performed on a population of patients undergoing PCI with DES to (i) determine the ability of the VERIFYNOW™ P2Y12 point-of-care assay (Accumetrics, Inc.) to distinguish between patients with and without subsequent post-discharge events, and to (ii) identify a clinically based threshold to determine the relative rates of events among patients with high and lower reactivity.

Platelet reactivity on clopidogrel therapy as measured with this point-of-care assay during the index hospitalization was found to be predictive of out-of-hospital outcomes after DES implantation, including stent thrombosis.

The optimal cut-off for the identification of high-risk patients was a PRU of ≥235; all CV deaths and stent thromboses occurred in patients with reactivity above this threshold. This cut-off point was similar to the boundary of the upper tertile of PRU in the population studied, which is consistent with previous observations that high post-clopidogrel reactivity is associated with subsequent CV events. The bootstrap estimation of the 95% confidence interval around the optimal cut-off was fairly wide, likely due to the low number of events that occurred in this study. Notably, the low range of the 95% confidence interval was still above the mean PRU in the population, which is consistent with previous findings that patients with residual platelet reactivity above the median around the time of PCI are at higher risk for subsequent events.

This example demonstrates a significant relationship between stent thrombosis and the presence of high post-clopidogrel platelet reactivity prior to the thrombotic event. The overall rate of subacute (0.8%) and late-stent thrombosis (0.8%) in the study is consistent with previous reports. Since platelet function assessment was performed prior to the thrombotic events, the data support the hypothesis that high post-clopidogrel reactivity is an etiological factor in stent thrombosis.

This example suggests that patients at risk for out-of-hospital ischaemic events, and in particular, stent thrombosis, may be stratified using a point-of-care platelet function assessment performed during the index hospitalization. Increased maintenance dosing regimens of clopidogrel can improve platelet inhibition in unselected patients and in diabetic patients at high risk for an impaired response. The third-generation thienopyridine prasugrel and other novel P2Y12 inhibitors may also be used to provide more potent and uniform P2Y12 inhibition.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All publications and patent applications cited in this specification are herein incorporated by reference as if each individual publication or patent application were specifically and individually indicated to be incorporated by reference.

The invention claimed is:

1. A method for measuring inhibition of platelet reactivity by a P2Y12 antagonist in an individual treated with a drug-eluting stent (DES), comprising the steps of:
   a) providing a platelet containing blood sample from an individual treated with a DES and a P2Y12 antagonist;
   b) contacting said platelet containing blood sample with particles comprising a GPIIb/IIIa receptor ligand immobilized thereon, adenosine diphosphate (ADP) and prostaglandin E1 (PGE1) under conditions suitable for agglutination of said particles mediated by said platelet in said blood sample; and
   c) assessing said agglutination to determine the presence, absence and/or degree of inhibition of platelet aggregation by said P2Y12 antagonist in said individual, wherein absence or a reduction of said agglutination indicates that said individual has reduced platelet reactivity in response to said P2Y12 antagonist treatment.

2. The method of claim 1, wherein the platelet containing blood sample is a whole blood sample.

3. The method of claim 1, wherein the platelet containing blood sample is a plasma sample.

4. The method of claim 3, wherein the plasma sample is a platelet rich plasma (PRP) sample.

5. The method of claim 1, wherein the P2Y12 antagonist is a thienopyridine.

6. The method of claim 5, wherein the thienopyridine is clopidogrel.

7. The method of claim 5, wherein the thienopyridine is ticlopidine.

8. The method of claim 1, wherein the individual is further treated with aspirin.

9. The method of claim 1, wherein the particles comprise polystyrene or latex.

10. The method of claim 1, wherein the particles comprise an infrared dye, the contacting step forms an assay mixture between the platelet containing blood sample and the particles, assessing the agglutination of the particles comprises irradiating the assay mixture with a light in the infrared spectrum and assessing the transmission of infrared light from the assay mixture.

11. The method of claim 1, wherein the GPIIb/IIIa receptor ligand comprises a substance selected from fibrinogen, monoclonal antibody 10E5, monoclonal antibody c7E3, von Willebrand factor, fibronectin, vitronectin, a ligand that has an arginine glycine-aspartic acid (RGD) sequence, a peptide that mimics the RGD sequence, or a peptidomimetic that mimics the RGD sequence.

12. The method of claim 1, wherein the GPIIb/IIIa receptor ligand is fibrinogen.

13. The method of claim 1, wherein the ADP has a final concentration of 2 to 35 μM and the PGE1 has a final concentration of 2 to 30 nM.

14. The method of claim 1, wherein the ADP has a final concentration of 15 to 20 μM.

15. The method of claim 1, wherein the PGE1 has a final concentration of 20 to 25 nM.

16. The method of claim 1, wherein the particles, ADP and PGE1 are contained in an assay medium.

17. The method of claim 16, wherein the assay medium has high absorption at about 800 nm.

18. The method of claim 1, which is conducted at a temperature ranging from 30° C. to 40° C., and the total time of the readings from the time of the contact among the platelet containing blood sample, the particles comprising an attached GPIIb/IIIa receptor ligand, ADP and PGE1 ranges from about 10 seconds to about 10 minutes.

19. The method of claim 5, wherein the thienopyridine is prasugrel.

20. The method of claim 1, further comprising assessing the risk level of the individual for stent thrombosis.

\* \* \* \* \*